(12) United States Patent
Lichorowic et al.

(10) Patent No.: US 9,008,628 B2
(45) Date of Patent: *Apr. 14, 2015

(54) INTERACTIVE VOICE ACCESS AND NOTIFICATION SYSTEM

(75) Inventors: Brian L. Lichorowic, Middleburg, VA (US); Xia Zhang, Sterling, VA (US); Kenneth George Aubey, Winchester, VA (US)

(73) Assignee: TBM, LLC, Bethesda, MD (US)

(*) Notice: Subject to any disclaimer, the term of this patent is extended or adjusted under 35 U.S.C. 154(b) by 282 days.

This patent is subject to a terminal disclaimer.

(21) Appl. No.: 13/369,158

(22) Filed: Feb. 8, 2012

(65) Prior Publication Data

US 2013/0077772 A1 Mar. 28, 2013

Related U.S. Application Data

(63) Continuation-in-part of application No. 12/367,416, filed on Feb. 6, 2009, now Pat. No. 8,131,267.

(60) Provisional application No. 61/054,460, filed on May 19, 2008.

(51) Int. Cl.
| | |
|---|---|
| H04M 1/663 | (2006.01) |
| H04M 1/27 | (2006.01) |
| G10L 13/04 | (2013.01) |
| H04M 3/493 | (2006.01) |
| H04M 11/04 | (2006.01) |
| G06Q 10/10 | (2012.01) |
| G06Q 50/24 | (2012.01) |
| G10L 13/00 | (2006.01) |
| G10L 15/26 | (2006.01) |

(52) U.S. Cl.
CPC ............. *H04M 1/271* (2013.01); *G10L 13/043* (2013.01); *H04M 3/4938* (2013.01); *H04M 11/04* (2013.01); *H04M 2201/39* (2013.01); *H04M 2201/40* (2013.01); *G06Q 10/10* (2013.01); *G06Q 50/24* (2013.01); *G10L 13/00* (2013.01); *G10L 15/26* (2013.01)

(58) Field of Classification Search
CPC ................. H04M 33/2281; H04M 2203/2016; H04M 1/271
USPC ..................... 379/88.02, 38, 88.22, 69, 88.04; 455/412.2, 421, 413, 41.2, 404.1; 370/260, 352; 600/301, 300
See application file for complete search history.

(56) References Cited

U.S. PATENT DOCUMENTS

| 2002/0098831 A1* | 7/2002 | Castell et al. ................. 455/413 |
| 2002/0168986 A1 | 11/2002 | Lau et al. |
| 2003/0119485 A1 | 6/2003 | Ogasawara |

(Continued)

FOREIGN PATENT DOCUMENTS

KR 10-2007-0066263 A 6/2007

*Primary Examiner* — Kiet Doan
(74) *Attorney, Agent, or Firm* — Seyfarth Shaw LLP

(57) ABSTRACT

An interactive voice access and notification method includes monitoring one or more notification events associated with one or more recipients identified by a user to detect a trigger of the notification event(s). The method also includes initiating a call to the recipient(s) in response to detecting the trigger of the notification event(s). The method also includes playing back an interactive audible notification message received from the user in response to confirming the recipient(s) are on the call. The method further includes sending a confirmation response to the user when a response from the recipient(s) to the interactive audible notification message triggers a confirmation response.

15 Claims, 14 Drawing Sheets

(56) References Cited

U.S. PATENT DOCUMENTS

| | | |
|---|---|---|
| 2004/0006478 A1 | 1/2004 | Alpdemir et al. |
| 2006/0276208 A1 | 12/2006 | Jain |
| 2006/0276210 A1 | 12/2006 | Thomas et al. |
| 2007/0032222 A1 * | 2/2007 | Koch .......................... 455/412.2 |
| 2007/0238453 A1 * | 10/2007 | Chang .......................... 455/421 |
| 2008/0095331 A1 | 4/2008 | Wlasiuk |
| 2008/0165937 A1 * | 7/2008 | Moore ....................... 379/88.04 |

* cited by examiner

INTERACTIVE VOICE ACCESS AND NOTIFICATION SYSTEM

CROSS-REFERENCE TO RELATED APPLICATION

This application is a continuation-in-part of U.S. patent application Ser. No. 12/367,416, filed Feb. 6, 2009, entitled "Interactive Voice Access and Retrieval of Information," which claims the benefit of U.S. Provisional Patent Application No. 61/054,460, filed May 19, 2008, entitled "System, Method and Computer Program Product for Interactive Voice Access and Retrieval of Information."

TECHNICAL FIELD

The present disclosure relates generally to automatic notification systems, and more particularly to an interactive voice access and notification system.

BACKGROUND

Various conventional platforms provide textual interaction with multiple information databanks. However, physical inability and multitasking have increasingly dictated the use of hands-free systems, such as voice response systems. While conventional resources such as the Internet (or World Wide Web) have provided users with a ready access to a wide array of information, accessing such information has conventionally required text-based queries. Similarly, other services accessible either through the Internet or from other sources generally require a user to interface using text based, keystroke commands. While voice response interfaces are available (e.g., subscriber's voice mail system), robust capabilities for information access is desirable. Furthermore, existing voice response interfaces are limited to a particular function, and are not readily adaptable to a user's information requirements. As society becomes more mobile (i.e., access to wireless communication) and more dependent on instantaneous dissemination of information, notification of important information with the ability to confirm receipt of the information using voice response is desirable.

For example, emergency responders (e.g., firefighters, search-and-rescue teams, or others) need to be contacted immediately to see who is nearby and available. Conventionally, such life-critical dispatching operations are left to human operators. Human operators contact the appropriate person and determine whether that person can respond to the emergency. However, human operators conventionally receive hundreds of phone calls with different emergencies that make it difficult to reach an emergency responder efficiently.

In other instances, conventional notification systems inform a user when an electronic mail ("e-mail") message was received and allows the user to read the message. Some conventional notification devices provide services that send stock updates, sport scores, weather alerts, traffic updates or other variable information to text-compatible communication devices. However, the message may not arrive to the intended recipient in a timely manner, because people can forget to carry their communication devices with them, or the communication devices can fail for any variety of reasons. Conventional services can determine whether the communication device received the notification, but ensuring that the intended recipient received the notification is desirable.

In still other instances, a recipient can very quickly be inundated with information that the recipient is not interested in. Conventional automated notification systems notify the recipient of all e-mail (e.g., on a store and forward basis) regardless of whether the message is unsolicited ("spam") or an expected message. Sorting through the unwanted messages with greater efficiency is desirable.

In some conventional approaches of communication, a user carries multiple communication devices. The user communicates with a combination of devices, such as a pager, a mobile telephone, a personal digital assistant (PDA), a two-way communication device (e.g., BLACKBERRY®), or others. However, having multiple communication devices makes it difficult to maintain each device in operating condition and affordable communication service.

In other conventional approaches, text-to-speech (TTS) technology provides users the ability to retrieve e-mail messages over the telephone by reading a text message to the user. However, the user must call in and sift through all the messages in the user's voice mailbox, so informing the user when a message has arrived is desirable.

Thus, what is needed is a solution for using voice-based communication to reduce dependency of text-based communication and increase assurance of information reaching recipients. The solution should permit interactive voice access and retrieval of information without the limitations of conventional techniques.

SUMMARY

According to one aspect of the present disclosure, an interactive voice access and notification method includes monitoring one or more notification events associated with one or more recipients identified by a user to detect a trigger of the one or more notification events. The method also includes initiating a call to the one or more recipients in response to detecting the trigger of the notification event(s). The method also includes playing back an interactive audible notification message received from the user in response to confirming the one or more recipients are on the call. The method further includes sending a confirmation response to the user when a response from the one or more recipients to the interactive audible notification message triggers a confirmation response.

According to another aspect of the present disclosure, an interactive voice access and notification apparatus includes a memory and one or more processors coupled to the memory. The processor(s) is configured to monitor one or more notification events associated with one or more recipients identified by a user to detect a trigger of the notification event(s). The processor(s) is further configured to initiate a call to the recipient(s) in response to detecting the trigger of the notification event(s). The processor(s) is further configured to play back an interactive audible notification message received from the user in response to confirming connection with the recipient(s). The processor(s) is further configured to send a confirmation response to the user when a response from the recipient(s) to the interactive audible notification message triggers a confirmation response.

According to another aspect of the present disclosure, a computer program product for interactive voice access and notification includes a computer-readable medium having non-transitory program code recorded thereon. The program code includes program code to monitor one or more notification events associated with one or more recipients identified by a user to detect a trigger of the notification event(s). The program code also includes program code to initiate a call to the recipient(s) in response to detecting the trigger of the notification event(s). The program code also includes program code to play back an interactive audible notification message received from the user in response to confirming connection with the recipient(s). The program code also includes program code to send a confirmation response to the user when a response from the recipient(s) to the interactive audible notification message triggers a confirmation response.

The foregoing has outlined rather broadly the features and technical advantages of the present disclosure in order that the detailed description that follows may be better understood. Additional features and advantages will be described hereinafter which form the subject of the claims of the disclosure. It should be appreciated by those skilled in the art that the conception and specific embodiments disclosed may be readily utilized as a basis for modifying or designing other structures for carrying out the same purposes of the present disclosure. It should also be realized by those skilled in the art that such equivalent constructions do not depart from the technology of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawings.

DETAILED DESCRIPTION

A detailed description is provided below along with accompanying figures that illustrate the principles of various embodiments. The scope of the embodiments is limited only by the claims and encompasses numerous alternatives, modifications and equivalents. Numerous specific details are set forth in the following description. These details are provided solely for the purposes of example and the embodiments may be practiced according to the claims without some or all of these specific details.

Figure 1:
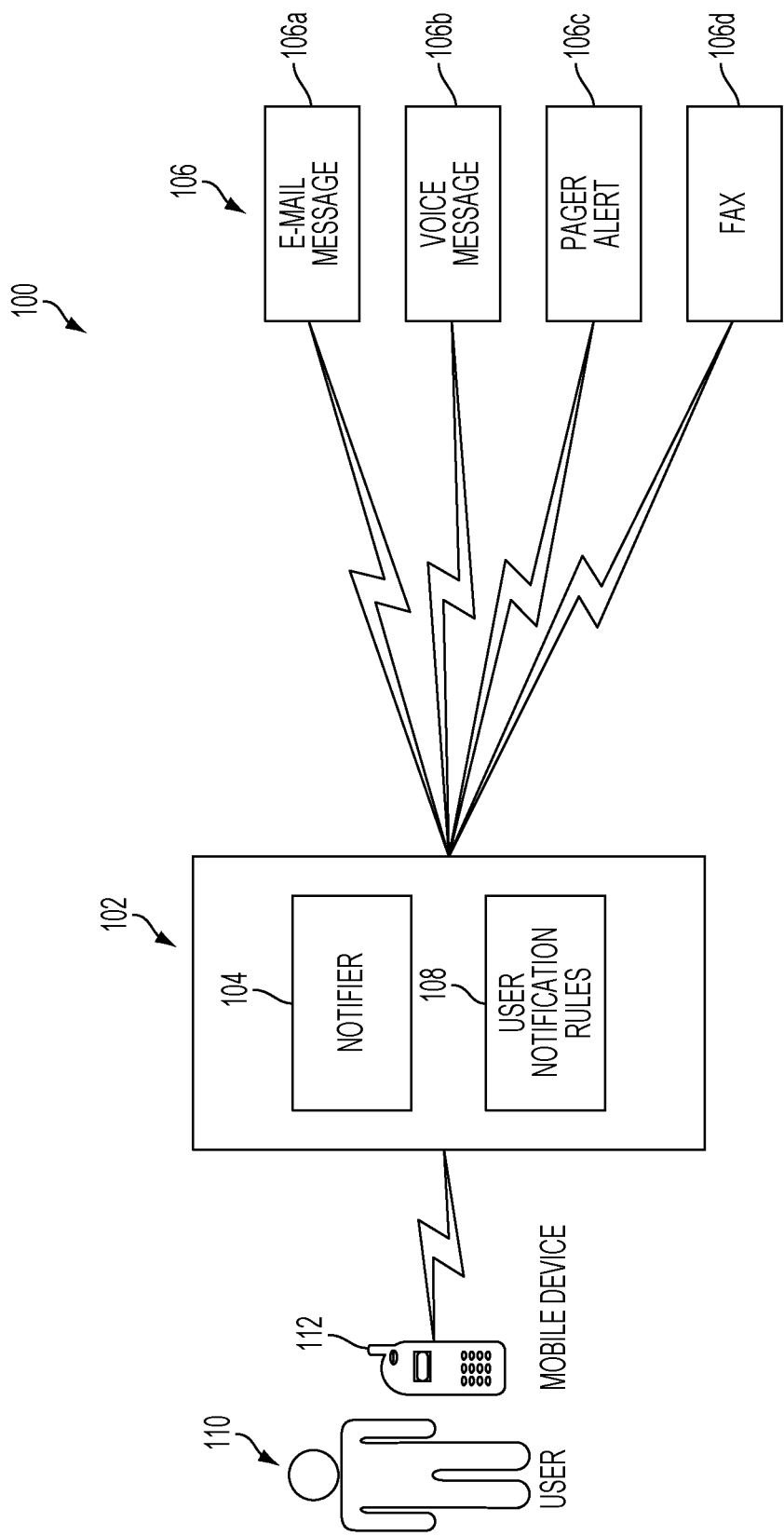
FIG. 1 is a diagram illustrating an exemplary notification system.

FIG. 1 is a diagram illustrating an exemplary notification system 100 having a computer system 102 with a notifier 104 functioning according to user notification rules 108. The notifier 104 receives notification events 106 selected at the option of the user 110. In some embodiments, the notifier 104 can receive notifications from services such as an e-mail message 106a, a voice mail message 106b, a pager alert 106c, or a fax message 106d all intended for the user 110. The notifier 104 has access to the user notification rules 108 which can define what types of events (e.g., receipt, change, update, alert, or notification of the service) should trigger a notification message to the user. In one example, a first rule may specify when those events should occur. In another example, a second rule may specify the source of the event. In still another example, a third rule may specify when to notify the user 110. In yet another example, a fourth rule may specify what telephone number of the mobile phone 112 to connect to in order to notify the user 110. In other examples, another rule may specify a time frame when the notification may reach the user 110. For example, the fourth rule might specify that the user 110 should be notified at a specific phone number between the hours of 2:00 p.m. and 4:00 p.m. today when the e-mail message 106a from John Doe is detected on the same day between the hours of 11:00 a.m. and 3:00 p.m. If the e-mail message 106a matches a rule from the user notification rules 108, then a notification is generated in response to the detection of the e-mail message 106a. As exemplified earlier, the fourth rule can allow the notifier 104 to contact the user 110 by phone at the specified number of the mobile phone 112. In other embodiments, the notifier 104 can ask the user 110 to interact with the notifier 104 verbally, when the user 110 answers the phone call. This interaction shows that a person (e.g., user 110) rather than an answering machine (not shown) has answered the phone call. The notifier 104 can also ask the user 110 to authenticate themselves as the intended recipient. For example, the user 110 may enter a key sequence to identify oneself, provide verbal identification, or may enter a personal identification number (PIN) via the telephone keypad. When the notifier 104 determines that the user 110 answered the phone call as intended and the entry provided matched the identity of the intended recipient, then the notifier 104 is alerted that the intended recipient (e.g., user 110) has answered the phone call. Following the authentication by the notifier 104, information about the event (e.g., receipt of service) or service (e.g., email, voicemail, page, fax, or others) can be played as a text-to-speech message to the user 110.

Figure 2:
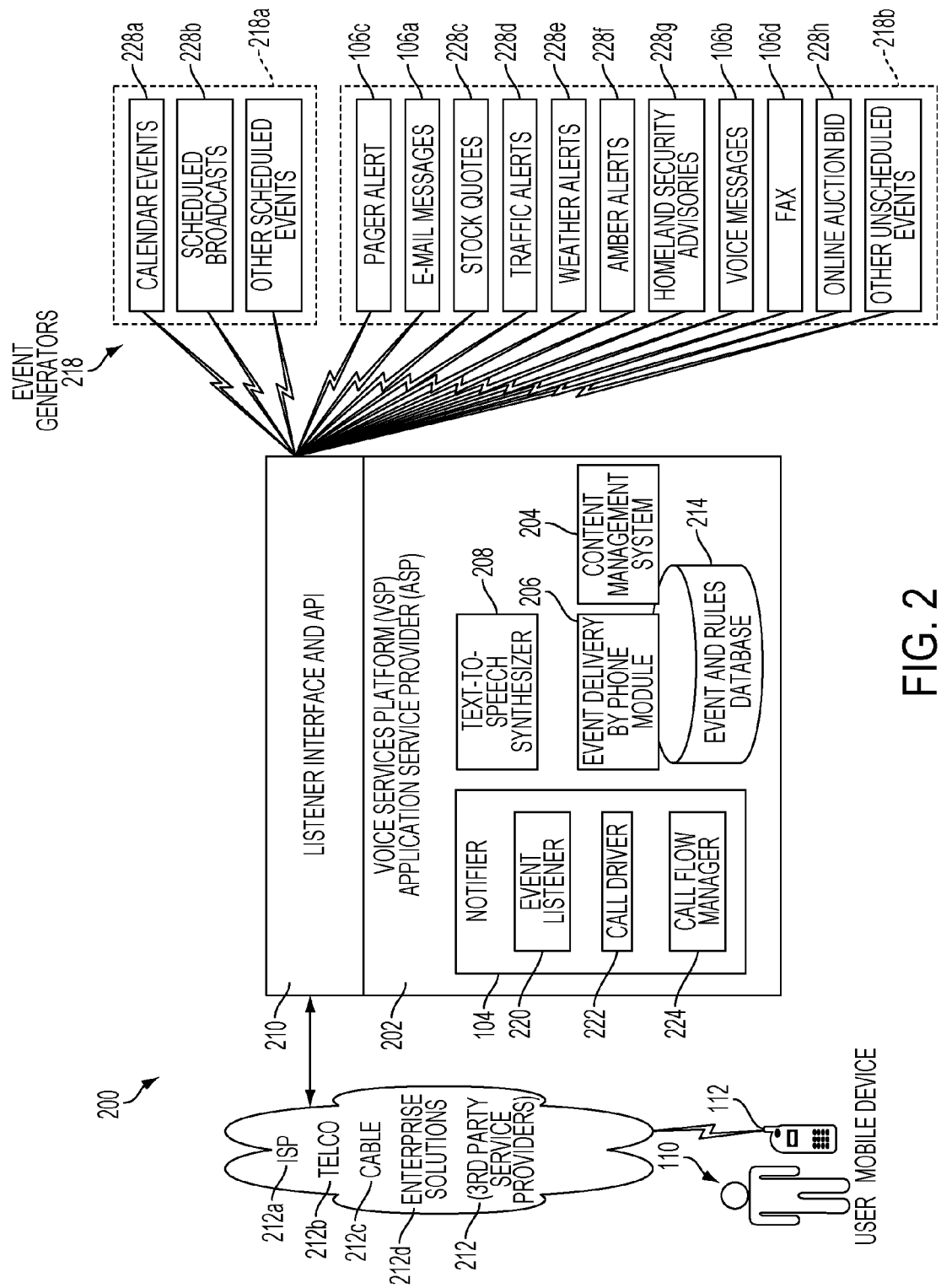
FIG. 2 is a diagram illustrating another exemplary notification system.

FIG. 2 is a diagram illustrating another exemplary notification system 200 with a voice services platform 202 that includes a content management system 204, an event delivery module 206, and an events and rules database ("event database") 214 connected to the content management system 204. Also, the voice services platform 202 is connected to a text-to-speech synthesizer module 208 for synthesizing textual data into verbal information. In one example, a notifier 104 as previously described in FIG. 1 interacts with both the content management system 204 and the text-to-speech synthesizer module 208. The notifier 104 informs a user 110 who may be in direct contact with a mobile phone 112 with information about event generators 218, which may provide information about services of interest to the user 110. In another embodiment, the voice services platform 202 can be configured as an application service provider, which includes an application programming interface (API) 210 that allow third-party service providers 212 to provide textual data into verbal information without having to develop their own systems. In some embodiments, the third-party service providers may include Internet service providers (ISPs) 212a, telephone companies (TELCO) 212b, cable companies 212c, enterprise solution providers 212d, or others of the like.

In one embodiment, the notifier 104 can include components (e.g., an event listener 220, a call driver 222 and a call flow manager 224) that generate and provide event notifications to the user 110. In another embodiment, the notifier 104 can provide notifications or alerts related to scheduled event generators 218a and unscheduled event generators 218b. In still another embodiment, triggers generated by event listener 220 can also detect calendar events 228a and scheduled broadcasts 228b. In still other embodiments, other triggers can detect a pager alert 106c, e-mail message 106a, stock quotes 228c, traffic alerts 228d, weather alerts 228e, "Amber" alerts 228f, homeland security advisories 228g, voice mail message 106b, fax message 106d, online auction bid alerts 228h, or other unscheduled events.

Figure 3:
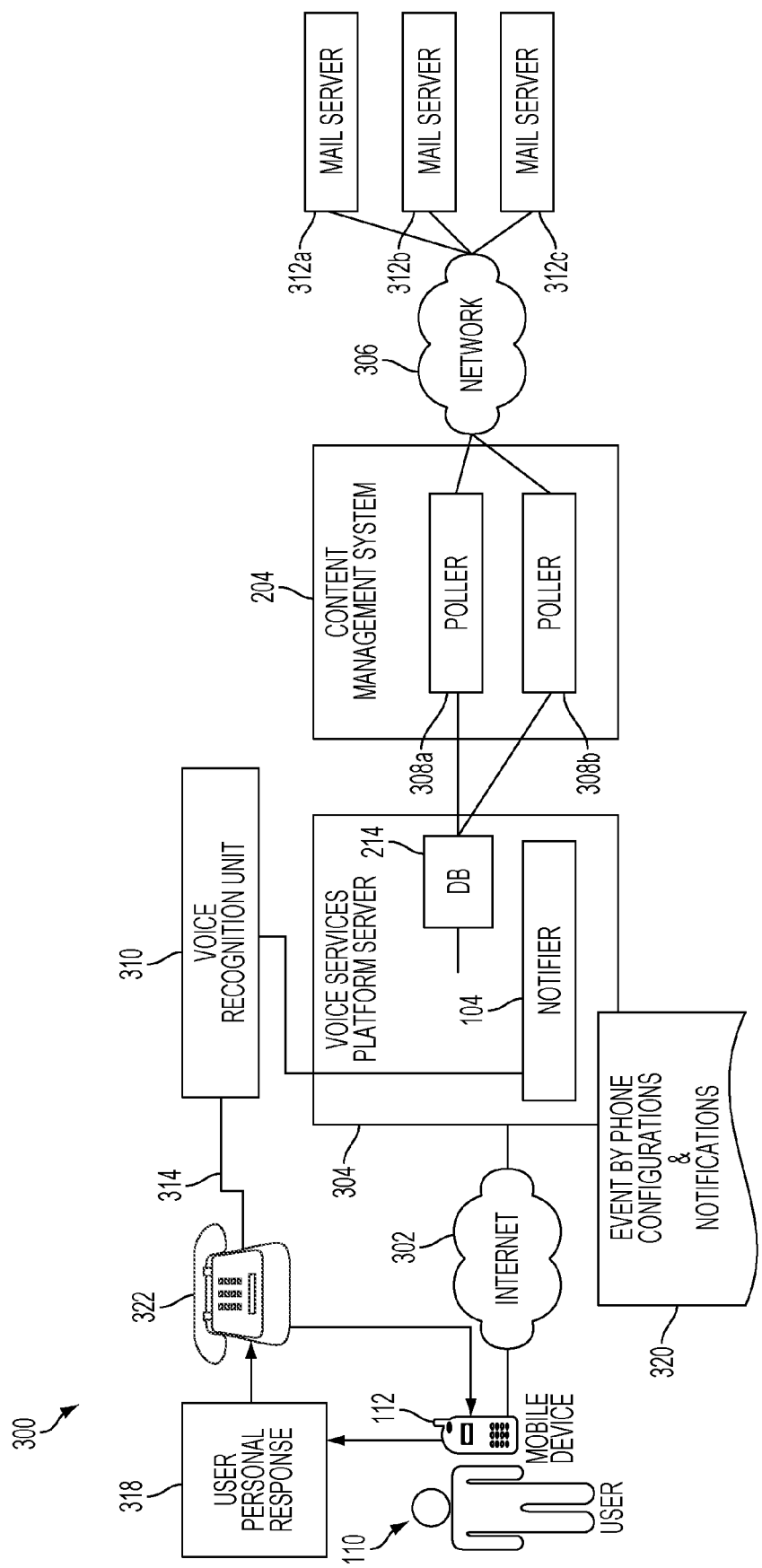
FIG. 3 is a diagram illustrating an exemplary interface to mail servers with a voice services platform.

FIG. 3 is a diagram illustrating an exemplary interface to mail servers with a voice services platform. Referring to FIG. 3 in conjunction with FIGS. 1 and 2, a user 110 connects to the Internet 302 intending to reach a voice services platform server 304 as part of notification system 300. The user 110 in communication with the voice services platform server 304, can configure one or more of user notification rules 108 (FIG. 1). In one embodiment, a rule belonging to user notification rules 108 can specify a type of event to detect. For example, an e-mail message 106a, a pager alert 106c, a stock quotes 228c, or an online auction bid alerts 228h can provide an event identifying a change, an update, a receipt, or other relevant action originating from the aforementioned services. Also, the user 110 can specify certain characteristics about the event for the notification system 300 to detect. For example, the characteristics to be detected can include a sender or an originator of the event, a time the event was sent, the subject of the event, the urgency level, or others. Further, the user 110 can specify a time period during which the receipt of the event took place. Finally, the user 110 can specify a date and time for notifications of the detected events to take place, and specify the phone number of the mobile phone 112 to reach the user at the specified date and time. In another embodiment, the mobile phone 112 may be configured to physically connect to a LAN phone line (i.e., not mobile as shown in FIG. 3). In still another embodiment, the user 110 can specify multiple phone numbers to contact at different time periods. In yet another embodiment, the voice services platform server 304 can store the user notification rules 108 in an event database 214 (FIG. 2). The user notification rules 108 can be accessed multiple ways. For example, the user notification rules 108 can be accessed by the user 110 over the Internet 302 using a web browser displaying input fields that allow the user 110 to create, review, update and delete the user notification rules 108. In another example, the user notification rules 108 can be assessed by the event listener 220 (FIG. 2) of the notifier 104 to identify events that may need out-bounding calls made. The content management system 204 can be connected to a network 306 that may include external access (e.g., Internet 302) or internal access such as a private network. In some embodiments, the content management system 204 can have pollers 308a and 308b, which can detect the event generators 218 (FIG. 2) with triggers. The pollers 308a and 308b can detect an e-mail message 106a (FIG. 1) from multiple e-mail accounts at mail servers 312a, 312b and 312c. The mail servers can originate from service providers such as Hotmail®, Yahoo!® mail, Google™ mail, AOL® mail, or any other electronic mail service provider.

In some examples, one of the pollers 308a and 308b can detect activity from event generators 218 such as receipt of an e-mail message 106a. The poller that detected the received email message updates the event database 214 with the email notification, which may include storing the email contents as well. The event listener 220 can compare the e-mail message 106a against the user notification rules 108, which can be stored in the event database 214. In other embodiments, the event generators 218 may be stored remote from the event database 214, but may be triggered by an external source, such as traffic alerts 228d or a weather alerts 228e. The event database 214 can store information about the event generators 218, and the information stored can be searched to find event generators that match the user notification rules 108. The notifier 104 can query the event database 214. For example, when an event generator from event generators 218 is matched to a rule of the user notification rules 108, then the notifier 104 can provide a voice recognition unit 310 with information of the event. The voice recognition unit 310 can then call the user 110 at the number specified by a notification configuration module 320 or the rule of the user notification rules 108. In other embodiments, the notification configuration module 320 can provide direction or control as to how the event may be provided to the user 110 by phone. Also, the voice recognition unit 310 can interact with the user 110 by having the user 110 respond to a prompt or verbal request to confirm that a person instead of an answering machine has answered the phone call. During the interaction between the voice recognition unit 310 and the user 110, the voice recognition unit 310 may request that the user 110 authenticate themselves. In another embodiment, a "Turing Test" can be presented to the user 110 visually or verbally in order to validate that the user 110 received the event notification first hand. When responses from the user 110 are deemed satisfactory, the voice recognition unit 310 can then proceed to transform text into verbal information about a first event intended for the user. The event database 214 can then be updated to reflect a status showing that the event notification or actual message was delivered to or retrieved by the user 110. In still other embodiments, interaction with that user 110 can be extended to include actions by the notification system 300 where such actions may include inserting bids based on online auction bid alerts 228h, perform stock transactions based on stock quotes 228c.

Figure 4:
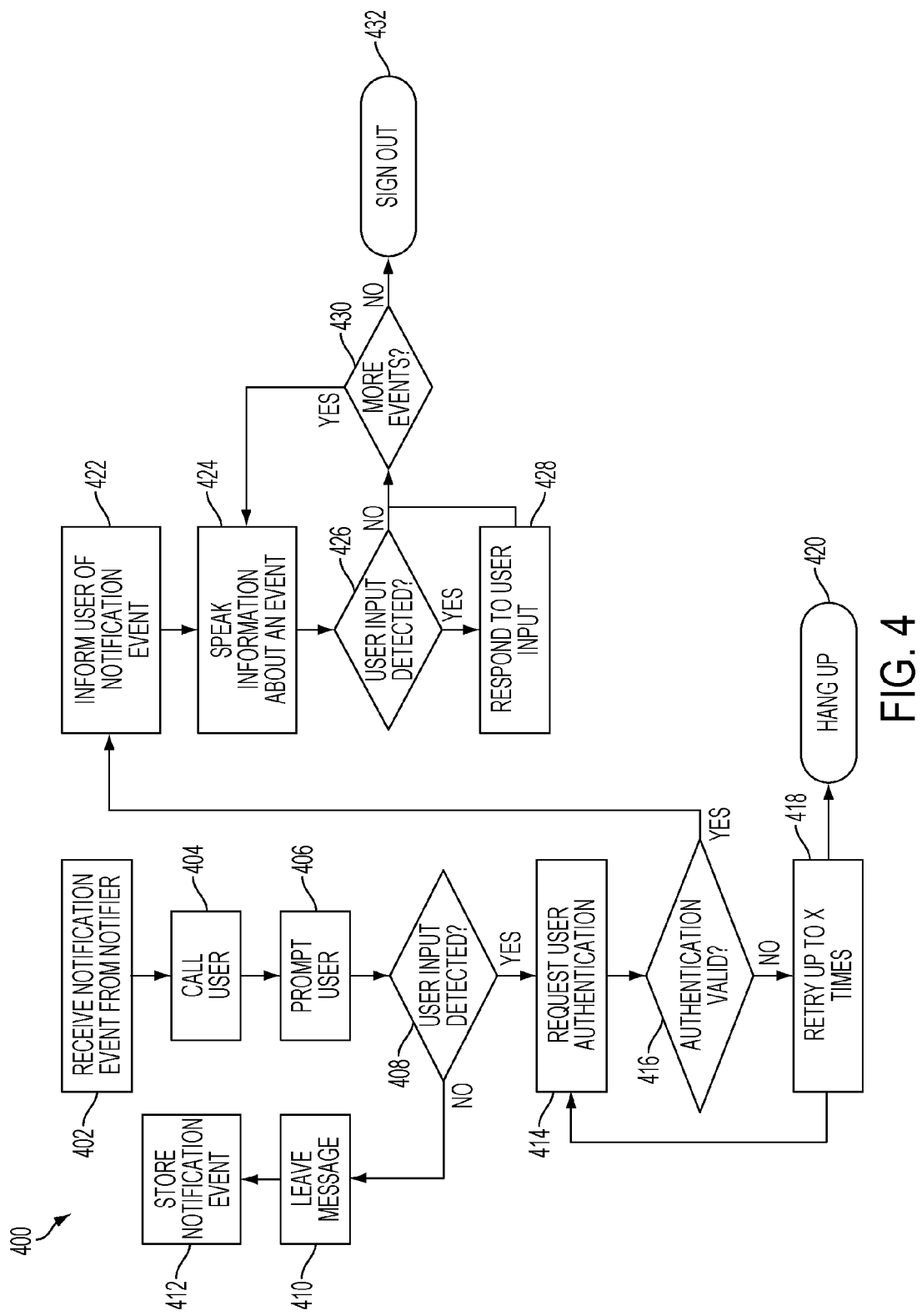
FIG. 4 is a diagram illustrating an exemplary call flow of an event notification receipt.

FIG. 4 is a diagram illustrating an exemplary call flow of an event notification receipt. Referring to FIG. 4 in conjunction with FIGS. 1 through 3, a call flow 400 depicts actions taken by the voice recognition unit 310 when interacting verbally with a user. For example, block 402 depicts the voice recognition unit 310 receiving the event generators 218 from the notifier 104. Block 404 depicts the voice recognition unit 310 calling the user 110 at a number specified in the user notification rules 108 as shown in 314 and 316 of FIG. 3. In block 406, when the mobile phone 112 is answered, the voice recognition unit 310 can prompt the user 110 for a user response 318 that confirms receipt of the event notification. The receipt confirmation may be activated by a key press, a Turing test, a specific password or phrase or any other desire activation generator. If no confirmation is received in block 408 within a specified period of time, the voice recognition unit 310 may assume that an answering machine or voice mail service has answered the call. Alternatively, the voice recognition unit 310 can leave a message in block 410, or take note that the caller was inaccessible and queue the call for retry. The message in block 410 can inform the user 110 about a received notification of the event generators 218 and provide a phone number 322 where the user 110 can call to retrieve information about the event at a later time. In block 412, the notification of the event generators 218 can be stored in a storage medium (e.g., event database 214) for later retrieval by the user 110.

If user input is detected at block 408, then the voice recognition unit 310 may prompt the user 110 for authentication information in block 414 such as, including but not limited to, a personal identification number (PIN) typed into the keypad of mobile phone 112, a spoken word, or spoken phrase identifying the user. If the provided user authentication information is determined to be invalid in block 416, then the user 110 can be prompted for the authentication information again in block 418 by repeating block 414 through block 416 until the authentication information is determined to be valid. The call can terminate in block 420. If the user 110 is unable to authenticate him or herself, then the voice recognition unit 310 can hang up the call as depicted in block 420.

The voice recognition unit 310 can attempt to reach the user 110 later for as many times as the user 110 has configured the notification configuration module 320 for retries. A failed recognition can be counted as one attempt to notify the user 110. The notifier 104 can have the flexibility to provide the user 110 an option to call back at the phone number 322 to check in with the system.

When authentication is valid in block 416, the user 110 can be informed of the notification event as shown in block 422. In one embodiment, information about the event including subject matter and sender information at block 424 can be spoken to the user 110. In block 426, the voice recognition unit 310 can wait for an input from the user 110. In some embodiments, the user 110 can interact with the voice recognition unit 310 by choosing to listen to the event information, skipping the event information, proceeding to the next event information, or hanging up the call. If the user 110 chooses to listen to information about an event, additional inputs from the user 110 can be entered at any time during the call. In another embodiment, a call can be managed by call flow manager 224. For example, the user 110 can choose an action that saves, replays, deletes, skips, replies, proceeds, or signs off from the system while the event is playing. When user input is detected (or received) in block 426, the voice recognition unit 310 can respond appropriately in block 424 and block 428 as necessary to speak about additional event information. At the end of the event, the voice recognition unit 310 can continue to wait for additional user inputs in block 426 until there are no more events to narrate to the user 110 as determined in block 430. When there are no more events, the user 110 can be signed out in block 432 and the voice recognition unit 310 can hang up.

Figure 5:
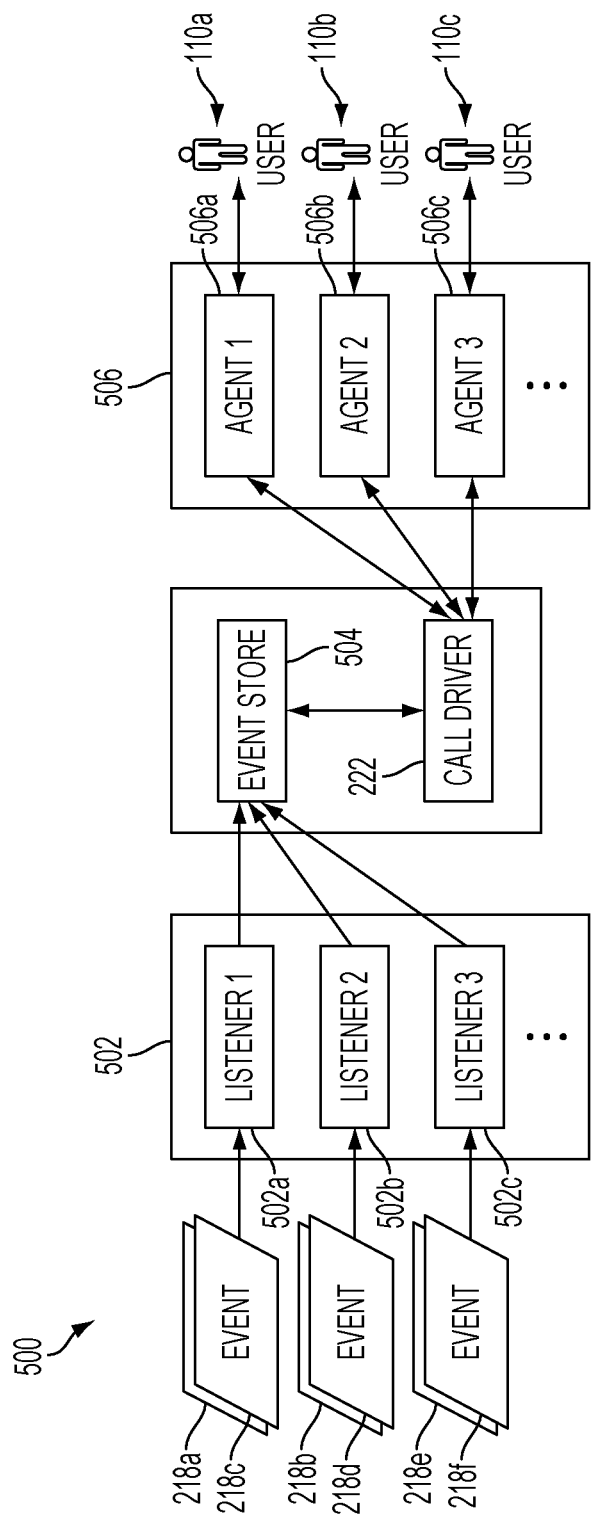
FIG. 5 is a diagram illustrating still another exemplary notification system.

FIG. 5 is a diagram illustrating still another exemplary notification system where the notification system 500 uses one or more of listeners 502a, 502b and 502c in a listener pool 502. In some embodiments, each of the listeners 502a, 502b, and 502c listens for one type of event. As a listener from the listener pool 502 receives an event, it can inform the event store 504 about the event. Referring to FIG. 5 in conjunction with FIGS. 1 and 2, the event store 504 can store information about the event and can push the event to a call driver 222. The call driver 222 can then forward the event to one of agents 506a, 506b, and 506c in an agent pool 506. An agent from the agent pool 506 can notify the user 110 (or multiple users) about the event. In some examples, the notification system 500 can receive inputs from a user 110a, where the user 110a interacts with the notification system 500 by responding to an online auction bid alerts 228h or other interactive service. In other embodiments, inputs from the user 110 can be communicated verbally through a voice recognition application over the mobile phone 112.

In some embodiments, the notification system 500 can be configured to dispatch a "call tree" of emergency responders. For example, homeland security advisories 228g can be provided to all the emergency responders having their methods of contact entered into the user notification rules 108. In the event of an emergency, the automated system can contact each responder (e.g. user 110a, user 110b, and user 110c) concurrently, and dispatch instructions for each responder in parallel. The notification system 500 may require interaction with the user to determine if the appropriate person has received the message. Information about the message delivery can be fed back to a dispatch center, which can then be displayed to a dispatcher. The dispatcher can determine how many responders are available and can stop the notification system 500 from contacting further responders when an appropriate number have been reached. Automating the dispatching service with parallel notifications to multiple users allows the dispatcher to receive more emergency calls from those in distress and greatly reduce response times. Other examples of the notification system 500 may include, but is not limited to notifying users and law enforcement officers of when a child has been abducted in their area.

In other embodiments, the notification system 500 can be configured to manage notifications regarding personal matters. For example, physicians' offices can automatically remind patients of appointments, and can offer the ability to reschedule. Airlines can automatically notify passengers when a flight is delayed or cancelled, and can provide the ability to reschedule. Users of online dating services or any other classified advertising service can be notified when someone responds to their ad and can be provided an opportunity to perform multiple actions such as respond to the response, request additional information, or schedule a meeting with the respondent. In other examples, financial companies can notify their customers when there is a problem with an account, such as an overdraft or unusual activity on the account. Commercial sales can also make use of the notification system 500. For example, a stock broker can automatically notify a customer when a stock of interest has dropped below a specified price and can allow the customer to purchase the stock. In another example, an on-line auction website can automatically notify a bidder regarding attainment of various bid objectives, such as when a maximum bid has been exceeded, or allow the bidder to increase their bid through the notification system 500.

The present disclosure can be used in many scenarios where the user 110 is expecting an event to occur and with the accessibility to a mobile phone (e.g., communication device, a computing device, a personal digital assistant (PDA), a mobile telephone, a multi-function voice enabled device, a voice-over-Internet Protocol (VoIP) device, or other mobile phones) is notified of the event's occurrence. The examples presented here are not meant to limit the implementations of the disclosure in any way but are intended to further illustrate exemplary embodiments according to the present disclosure.

Figure 6:
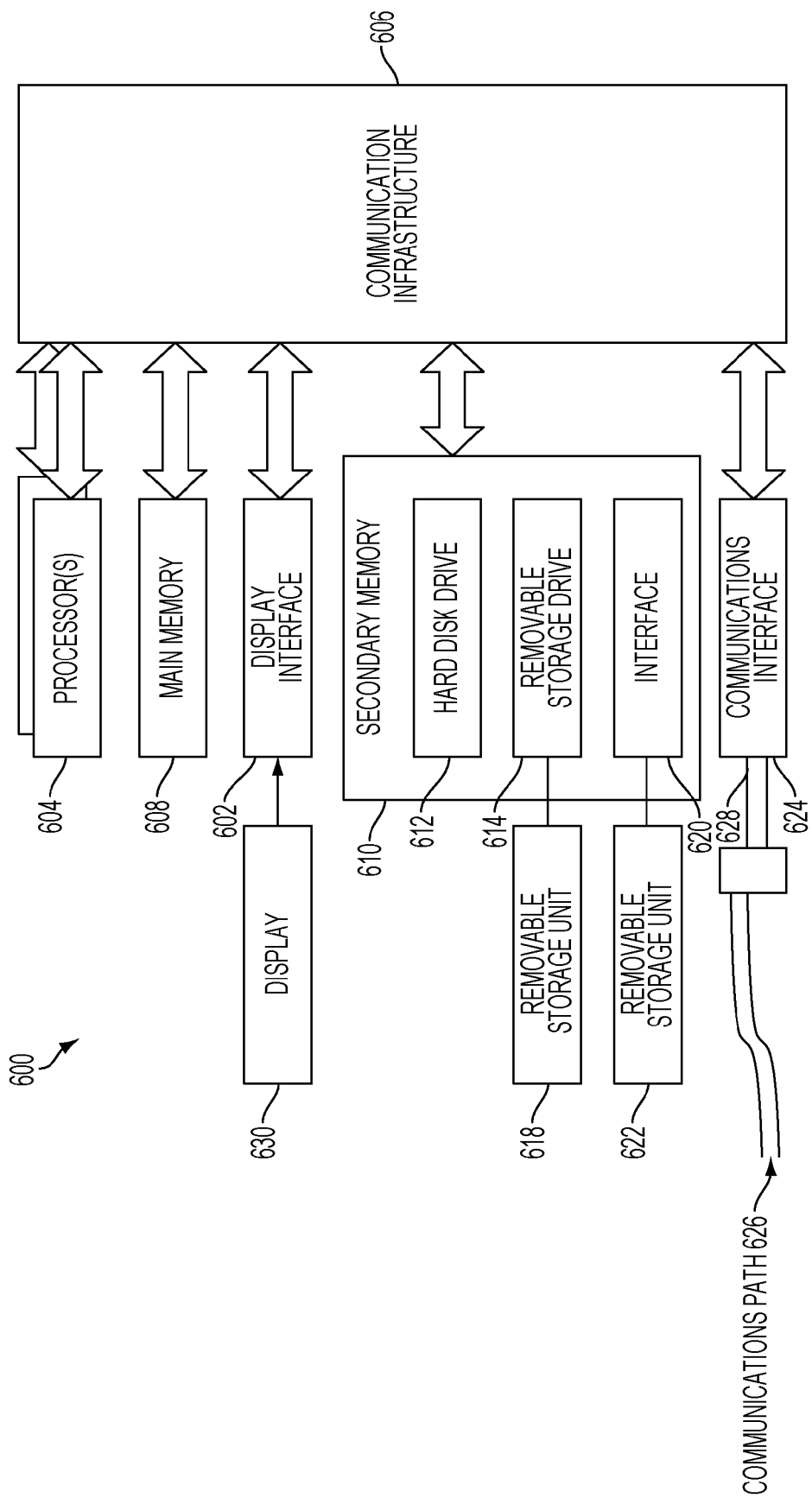
FIG. 6 is a diagram illustrating an exemplary computer system with various computing and communications devices.

FIG. 6 is a diagram illustrating an exemplary computer system with various computing and communications devices. Referring to FIG. 6 in conjunction with FIGS. 1 through 5, a computer system 600 includes interfaces to devices such as a mobile phone 112; a voice services platform server 304; a content management system 204; mail servers 312a, 312b, and 312c; a voice recognition unit 310; pollers 308a and 308b; a text-to-speech synthesizer module 208; an event delivery module 206; listeners 502a, 502b, and 502c; a call driver 222; event store 504; and agents 506a, 506b, and 506c. The present disclosure (or any part(s) or function(s) thereof) may be implemented using hardware, software or a combination thereof and may be implemented in one or more computer systems or other processing systems. In one embodiment, the disclosure is directed toward one or more computer systems capable of carrying out the functionality described herein. For example, computer system 600 can be configured as a personal computer (PC) system running an operating system such as, e.g., Windows 98/2000/XP, Linux, Solaris, OS/2, Mac/OS, or UNIX. In other examples, the computer system 600 can be implemented on any appropriate operating system, such as Solaris, Linux, HPUX, OSF, Windows 98, Windows NT, OS/2, Mac OS, and any others that can support Internet access. In another embodiment, the computer system 600 may be implemented on a computer system operating other components, such as a computing device; a communications device; a telephone; a personal digital assistant (PDA); a pocket personal computer; a handheld personal computer; client workstations; thin clients; thick clients; proxy servers; network communication servers; remote access devices; client computers; server computers; routers; web servers; data, media, audio, video, telephony, or streaming technology servers could each be implemented with the computer system 600 as shown in FIG. 6.

In some embodiments, the computer system 600 can include an input device such as a mouse or other pointing device of the like (e.g., a digitizer), and a keyboard or other data entry device of the like. The computer system 600 can implement output devices including, but not limited to, a display 630, and a display interface 602. The computer system 600 can include input/output (I/O) devices such as, a communications interface 624, a cable 628 and a communications path 626, which each can be connected to a network interface card, or a modem. The communications interface 624 allows software and data to be transferred between the computer system 600 and external devices. Some exemplary devices that are connected to the communications interface 624 may include a modem, a network interface (e.g., an Ethernet card), a communications port, a Personal Computer Memory Card International Association (PCMCIA) slot and card, or of the like. Software and data transferred via the communications interface 624 are in the form of signals, which may be electronic, electromagnetic, optical or other type of signal capable of being transferred across the communications interface 624 using the cable 628. The cable 628 links to the communications interface 624 via the communications path 626. The communications path 626 can carry electronic signals via the cable 628, fiber optics, a telephone line, a radio frequency (RF) link, or other types of communication channels.

In some embodiments, computer programs may include object oriented computer programs, which are stored in either the main memory 608 or the secondary memory 610. In other examples, the objected oriented computer programs may also be stored in a removable storage drive 614, which generally refer to computer program products. Such computer programs, when executed, enable the computer system 600 to perform features of the present disclosure as discussed herein. In particular, the computer programs, when executed, enable the processor 604 to perform the features of the present disclosure.

In other embodiments, the disclosure is directed to a computer program product including a computer-readable medium having control logic ("computer software") stored therein. The control logic, when executed by the processor 604, causes the processor 604 to perform the functions of the disclosure as described herein. In still other embodiments, the computer software may be stored in a computer program product and loaded into the computer system 600 using the removable storage drive 614, hard disk drive 612 or communications interface 624. The computer software can run as a standalone application running atop an operating system, or can be integrated into the operating system.

In still other embodiments, the computer system 600 includes one or more of processor 604. The processor 604 is connected to a communication infrastructure 606 (e.g., a communications bus, cross-over bar, or network). The computer system 600 can include the display interface 602 that forwards graphics, text, and other data from the communication infrastructure 606 (or from a frame buffer, not shown) for presenting on the display 630. The computer system 600 can also include a main memory 608, such as random access memory (RAM), with a secondary memory 610. The secondary memory 610 can include either a hard disk drive 612 or a removable storage drive 614, which represents a floppy diskette drive, a magnetic tape drive, an optical disk drive, a compact disk drive CD-ROM, or of the like. The removable storage drive 614 either reads from or writes to a removable storage unit 618 in a well known manner. The removable storage unit 618 which can be referred to as a program storage device or a computer program product is accessed for reading and writing by removable storage drive 614. In some embodiments, the removable storage unit 618 includes a computer-readable storage medium that stores computer data and instructions.

In yet another embodiment, the secondary memory 610 may include other similar devices for allowing computer programs or instructions be loaded into the computer system 600. For example, a removable storage unit 622 and an interface 620 may provide an alternative storage capacity. Examples of such may include a program cartridge and cartridge interface (e.g., those found in video game devices), or a removable memory chip (e.g., an erasable programmable read-only memory (EPROM), programmable read-only memory (PROM) with associated socket), which allow either data or instructions to be transferred from the removable storage unit 622 to the computer system 600. In some examples, hardware components such as application specific integrated circuits (ASICs) or other integrated circuits can implement one or more portions of the computer system 600 to provide functionality as described herein. In other examples, the computer system 600 can be implemented in a combination of both hardware and software components.

The disclosure may be used, for example, in conjunction with a product registration system. In one example, a manufacturer may use the notification function of the present disclosure to inform registered customers of new product features, product defects or recalls. Similarly, customers may be notified when the warranty on a registered product is about to expire, with the option to purchase extended warranty coverage.

In another example, the notification function may be integrated into a voice-responsive product registration system. Such a system may allow a product purchaser to call into an automated, voice-responsive system to register the purchased product. The purchaser may be presented with any number of questions about the product purchased, product preferences, personal interests, or of the like. The purchaser's verbal responses may be captured and stored in a database. A response to the questions may trigger an event notification.

For example, if the purchaser indicates an interest in a complementary product, a notification may be sent to a sales agent about the complementary product to follow-up with the purchaser. In another example, the purchaser may indicate an interest in features that are not yet available, and a notification may be sent to the purchaser when those features become available.

In other examples, the notification function may be used in conjunction with a broadcast voice notification system that may speed and simplify the notification process. The broadcast voice notification system "pushes" important information or notices to individual recipients with security, delivery authentication, and single-point activation. The broadcast voice notification system's secure voice alert administration is easy and intelligent, and may allow the user to select people to notify and to make choices on-the-fly, even to monitor who has been contacted moment by moment.

The broadcast voice notification system may provide a simple web interface, which may allow a phone list to be instantly created or recalled, a message to be typed (or pasted), and sent to many people simultaneously. The broadcast voice notification system may provide a seamless broadcasting system that gets a message delivered quickly. The broadcast voice notification system may contact all the people on a list at once, and reading the message to them when they answer the phone. The user who originates the message may monitor its broadcast in real-time through a computer-based user interface. The user interface may show if a call attempt fails, and the user may then try again at the appropriate time.

Figure 7:
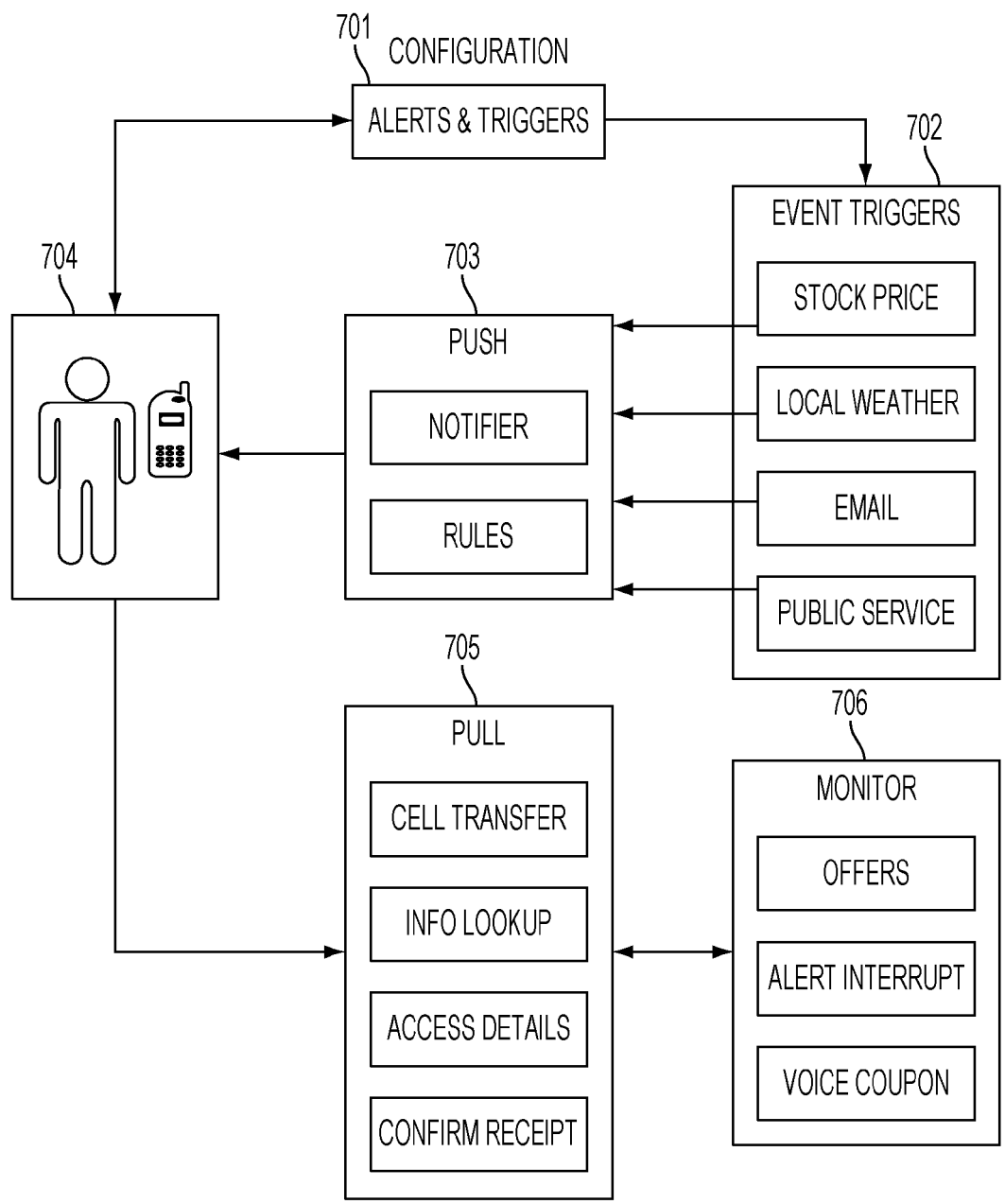
FIG. 7 is a flow diagram illustrating an exemplary interactive voice communication application.

FIG. 7 is a flow diagram illustrating an exemplary interactive voice communication application. With reference to push configuration 701, configuration data with alert triggers set by a user 704 are compiled and organized to establish an audible alert or an audible announcement of one or more events. For example, event information may include a stock price change, weather alerts for a particular region by zip code, an email message based on words or phrases in the subject field, public service announcements, or "Amber" alerts including other emergency related notifications. One or more of these configurations may be established by a user, where the user configuration data is pulled (i.e., to obtain from the user 704) and fed into an event trigger module 702 by using a pull mechanism 705 residing on a suitable platform. The platform may have the capability to periodically or continuously monitor source data received from, for example, a Really-Simple-Syndication ("RSS") feed (or a web feed), National Weather Service, emails that are monitored and other events and locations for events and based on preset user preferences. For example, if a stock price drops below a particular trigger, this may initiate an event that goes into a push mechanism 703 that includes a notifier 703*a*, but before alerting a user, the push mechanism 703 may implement a set of rules shown in rules 703*b* that allow the system to determine how to contact that user including rules (e.g., such as not to be alerted after 2:00 am). The rules 703*b* may also specify different places to notify a person, (for example, being able to provide more than one phone number, a Skype address), and/or different ways of contacting a person so alternative notification schemes and mechanisms may be used to connect to a user. Once the rules 703*b* have been determined, then the notification is forwarded on to the user 704. According to one embodiment, notification may be accomplished by a telephone such as a mobile phone, a land line, a Voice-over-IP (VoIP) phone, Skype, Vonage, or others. Other rules may specify that, if a person has an "X-Box Live" account and they are on line, the system may notify them by breaking in on their "X-Box Live" connection as opposed to calling them on the phone. As a result, the user 704 receives a notification. The system may read the notification to the user 704 (i.e., provide an audible notification) using text to voice services and then the user is allowed to react and interact with the system. At this point, the system provides further enhanced functionality over other systems, such other systems typically being limited to calling a party and providing limited, preprogrammed interactivity such as saying to "please hold for a representative", or "hit one (1) to be transferred to an agent" to make, for example, an online payment. Instead, once a person is on the phone and connected into the system, processing continues at the pull mechanism 705 to provide enhanced interaction with the user. For example, the user may be provided with the opportunity to initiate a verbal command to obtain "411" information services. The system can then look up a name and transfer the call to that number. In other situations, the system can look up information such as a stock price and then look up additional stock information so that a user can then decide whether to buy or sell. Accessing details, for example in response to an "Amber" alert, the system may inform a user that something has happened and that he or she is currently in the effected area. If the user is not traveling, for example, he/she may ask the system to provide them with the complete message. Alternatively, the user may ask to be connected to the local sheriff's office or whatever is necessary to further interact and connect with the end users. The user may further confirm receipt of the message using a variety of methods. For example, the person may be prompted to simply hit a key to confirm that they have received a message or to speak the confirmation, even to require that the person speak a secret password, such as, for example, in a municipal setting or government emergency scenarios where there is the need to enhanced confirmation and security. According to another embodiment, the user may be prompted to give a code phrase to indicate that a responsible party has received the outgoing message to provide a suitable level of system tracking and accountability. The potential for implementing a confirmation feature provides a significant ability to interact and connect the person into a major application side of the voice terminal service that a person normally dials into. At this point, a user may be given full access to the menu systems including the ability to check their email, ask for weather for different locations, stock prices, look up news feeds or access and retrieve any other information that is accessible by the system such as using the Internet. Thus, the system does not merely provide notification to a user but may provide the user with a complete interactive application with voice prompted and activated capabilities and resources.

A monitor mechanism 706 monitors the location of a calling party, e.g., the user 704. This allows the system to monitor and access the nature of the message being received and provide appropriate location-sensitive or responsive services such as a "411" system and to look up numbers and provide context relevant notification (e.g., location, time-of-day, user profile related, or others.) during an interactive call with a user. Thus, the system may not require a user to hang up and thereby provide another notification, but instead, while monitoring the persons current session, the system may provide other relevant services. So, for example, if a user is looking-up restaurants, the system can offer them a voice coupon and notify the person that, for example, a particular nearby restaurant is offering a special deal right now and provide an option to connect the user to the establishment and give them the coupon offer. In doing so, the system may also initiate a call to that restaurant, let the restaurant staff know that someone is on the line that is asking for the coupon offer and then connect the call. According to another embodiment, the system may offer a voice coupon, and ask the user to confirm, e.g., "would you like the coupon?" In response to an affirmative verbal reply, the system may email that coupon to the user or email the user a link to where they can register to receive the coupon. According to another embodiment, the system may take user registration information using a voice-registration functionality to take the person's complete name, address info if necessary, and/or pull it out of the system (e.g., perform a "look-up".) The system may further register all of that person's interests and for example, put them on a mailing list, to mail them a free sample of an associated product.

Figure 8:
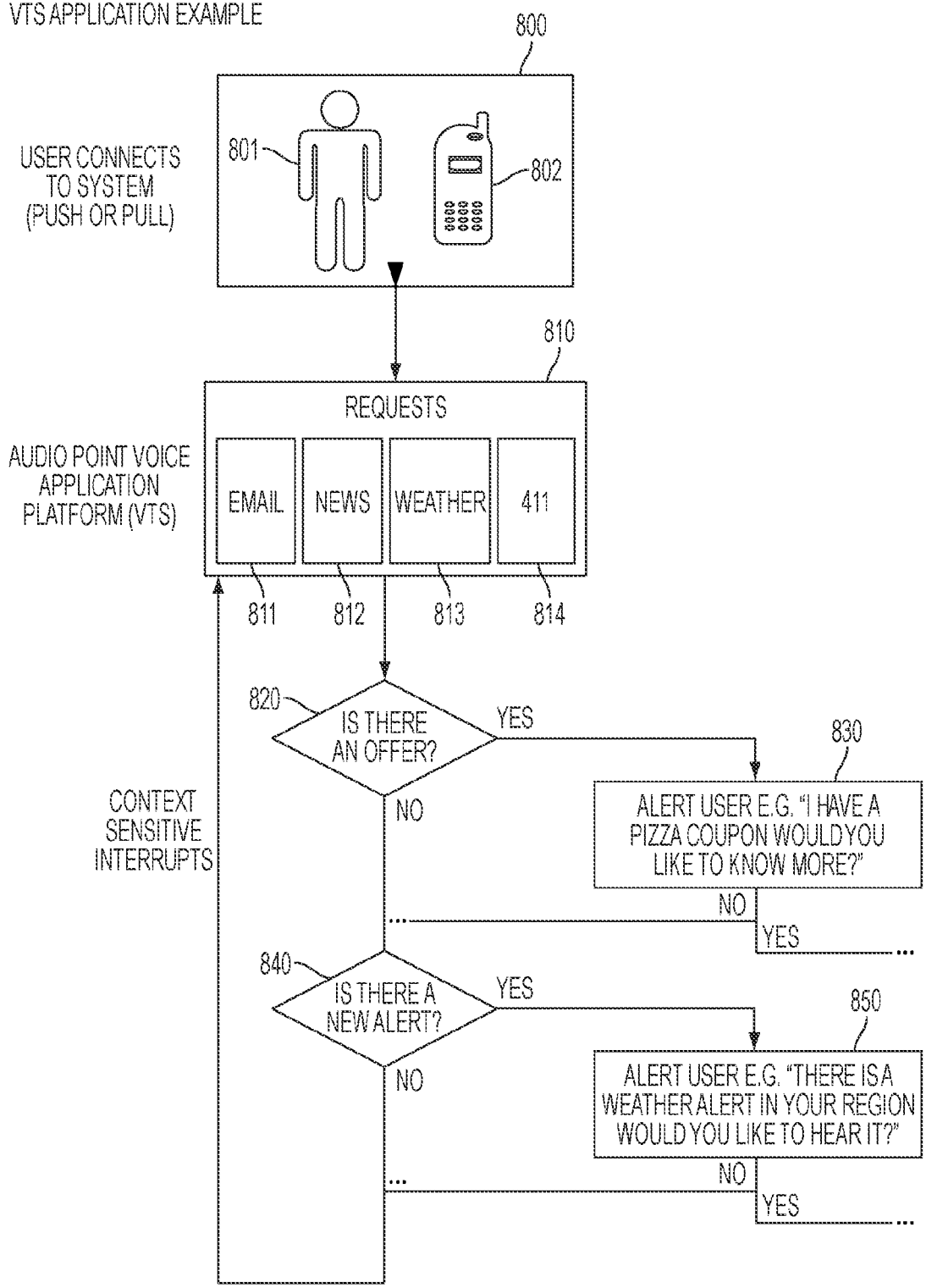
FIG. 8 is a flow diagram illustrating an exemplary interactive voice communication application including context sensitive interrupts.

FIG. 8 is a flow diagram illustrating an exemplary interactive voice communication application including context sensitive interrupts. Here, flow 800 has the user 704 (FIG. 7) initiates a connection to the system by, for example, a telephone. Once a connection with the system is established, processing continues at block 810 where the user interacts with the voice application platform and a voice terminal service providing the capability for the user to make their various requests. For example, the system may provide access to email 811, news 812, weather 813, directory 814 or any of a number of other information services accessible by the system (e.g., corporate databases, "Amber" alert or different kinds of agent lookup information such as arrest records for officers). As the user is connecting through the system, block 820 attempts to identify data the user is requesting and determine if there is a system match to different kinds of offers. For example, if a person requests news for their local area, as the system retrieves the news, the voice response system may inform the user of associated features and offers, i.e., "Hey, I have a special offer for a Ditimove in this area, would you like to know more?" If the user responds in the affirmative then processing continues in an interactive method, informing the user about what is going on and asking if they would like to know more. If the user responds in the negative, processing continues at block 840 or the system alerts the user as to the details of an alternative offer. Thus, normal processing is temporarily interrupted to offer the user some context relevant option after which the system comes back in and continues delivering the news or other originally requested information.

Returning to block 840, the system once again looks at alerts and so again with reference to the instant example and context, a user may be doing a "411" lookup for a particular area, e.g., requesting weather for a particular area, news based on a zip code, or others. Alternatively, if the system knows a person's default area, it may look to see if there is an alert, either based on user preferences or some sort of emergency indicated to be associated with the particular geographical area of the user. If there is an alert, processing may continue at block 850, where an appropriate voice message may be generated to the user, e.g., "There is a weather alert for your region, would you like to hear it?" If they say, "No", then the system may continue back into the interactive system, allowing the user to continue retrieving news or request new information. Alternatively, if the answer is, "Yes", the weather alert is instead provided after which the user is returned back into the system. While, this system of context sensitive interrupts may be provided on the web to provide context sensitive ads using various web pages, embodiments of the present system may read the text based information on a web page to provide context sensitivity with voice interaction with the user being offered context sensitive mechanisms based on their location and other factors while the system is retrieving data in a voice application.

Figure 9:
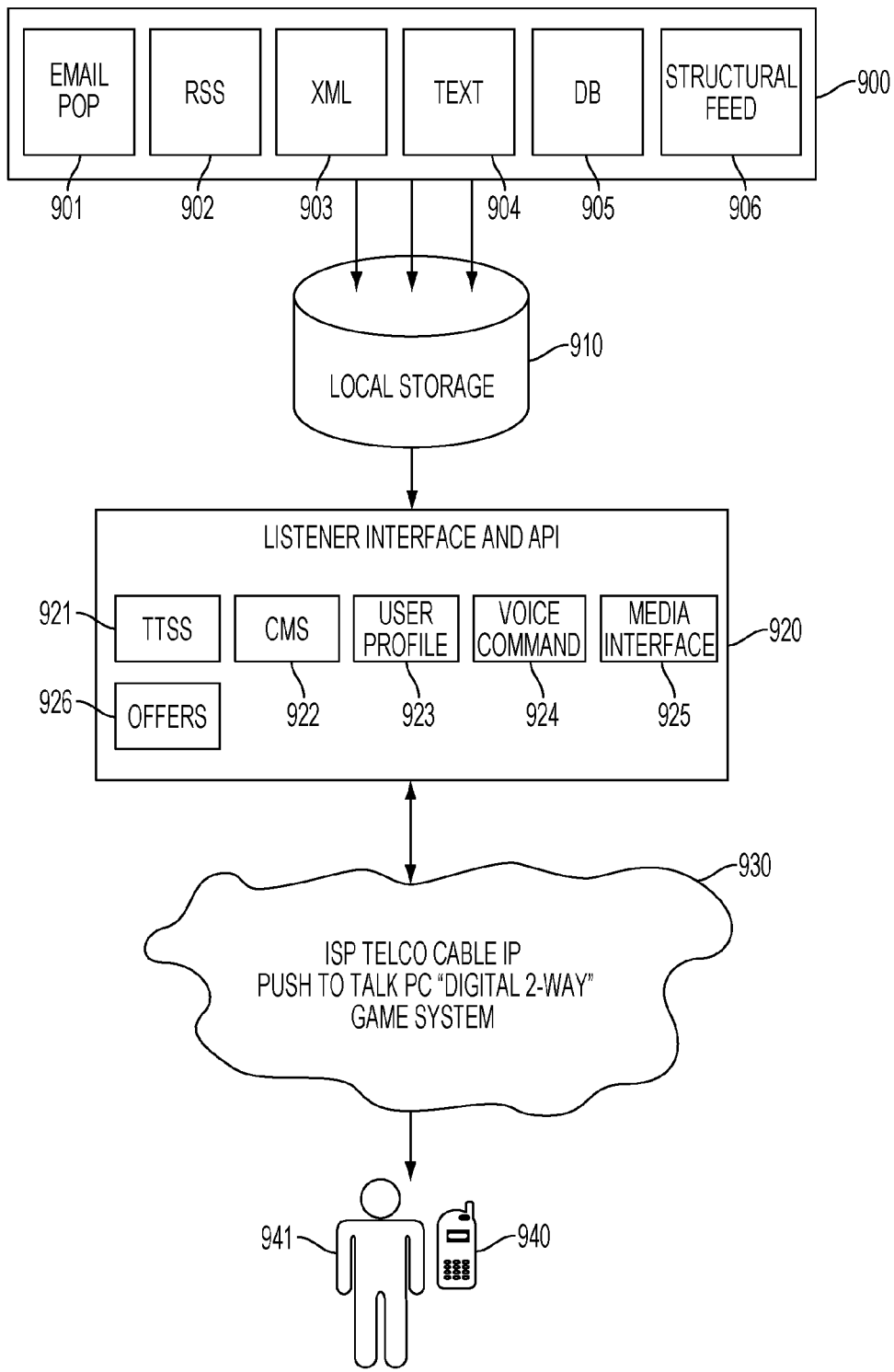
FIG. 9 is a flow diagram illustrating an exemplary interactive voice communication application including dependencies.

FIG. 9 is a diagram illustrating an exemplary flow of an interactive voice communication application including dependencies that may be made applicable regardless of whether interaction is based on an incoming or outgoing connection. At 900, various input sources are made accessible, accomplished, i.e., including, for example, email in POP, RSS, XNO, text feeds, a direct connection to a database, structured feeds, which might come from, for example, stock services, pager services, traffic alerts, weather alerts, "Amber" alerts, homeland security connections, local municipal event management systems, voice messages that may be connected into with different phone companies, faxes, online bid information and most types of structured data feeds. Preferred embodiments may be designed to implement a data access technology wherein web pages are useful as a means to access underlying structured data. The structured data is pulled into local storage that may be in the form of a local database. Having the data stored locally on the system may be more efficient. A database 920 can be implemented as a local storage with a general listener interface (or API). Also, the database 920 may interact with components such as text to a speech synthesizer 921 for reading data to a user 941. In some embodiments, a context management system 922 (or portion thereof) may behave like a user profile engine to provide data in relationship to an individual user profile so that what is being delivered and how the data is grouped together is responsive to the type of data, be it mapped by subject or perhaps it is by zip code or by key words that the user has specified. Thus, the context management system 922 provides a structure for how the data is arranged for rapid retrieval later on. User profiles 923 incorporate user preferences including the user information as previously described plus additional demographic information made available to the system and used to provide users with special notices such as weather alerts that may occur while the user is on the phone or perhaps for a notifier setting. Information that would allow the system to provide the user with a voice coupon and similar features may also be provided. Voice commands 914 may be utilized, available voice recognition technology and platforms such as, but not limited to voice commands and responses from the user are provided by a suitable voice connection processed by a voice command system 924 and compared against a set of capabilities so as to initiate appropriate action. Offerings 926 may be a local database of offers and participation rules for various offers. This may include such items as coupons, special data related to coupons, special commercial offers and other things that might be offered to an end user. A media interface engine 925 provides access to a communications interface 930 and may use various methods of connecting to an end user (e.g., IP connections over an ISP, an HM connection, SIP, traditional time-division multiplexing (TDM) Telco, hard line, mobile phone, Voice-over-IP, cable technologies, other types of internet protocols, push to talk interfaces, and/or PC-based systems such as (Skype or Vonage). Such functionality may also provide a backup method for notification for emergency response units using, for example, a digital two-way to connect to a user and further allowing the user to initiate a connection to the system, e.g., to look up pertinent information. Such functionality may also be supported by game systems, which may offer the capability for voice interaction. The interface to such systems may be made available on the Internet. In such case, a user currently playing a game and logged into a game network may be provided with an interface to provide them with pertinent alerts or allow them to interrupt their current system and interact with embodiments of the present system that may also be available to retrieve information. A two-way device 940 (or mobile phone 112 of FIG. 1) provides interaction between the user 941 and is the communications interface 930 to receive voice messages and other voice-based information. Although this may be a phone, different types of mechanisms may be used to connect to the end user. Embodiments of the system preferably include a voice enabled platform providing suitable voice quality.

Figure 10:
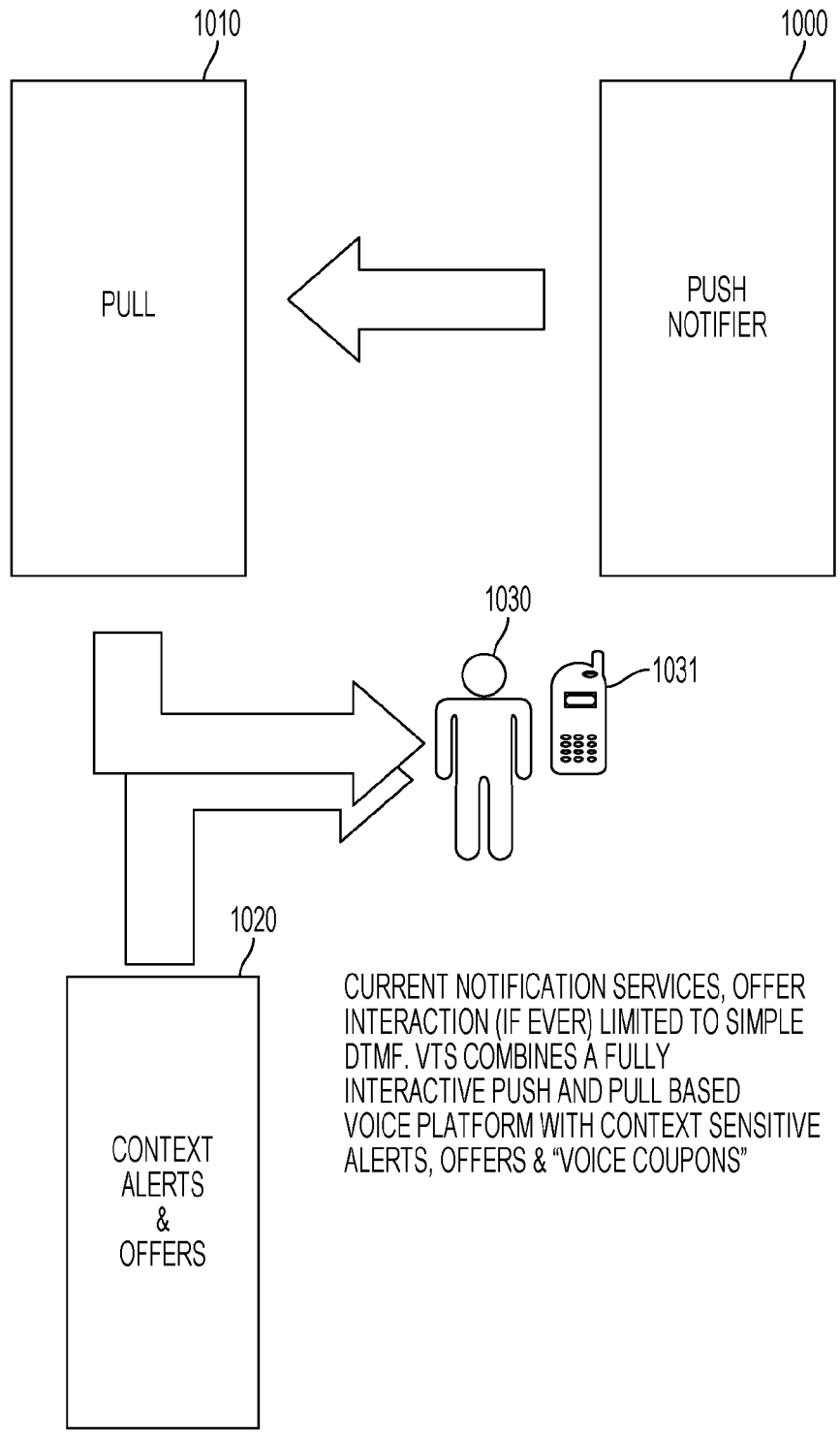
FIG. 10 is a diagram illustrating an exemplary user interaction with a voice terminal service platform.

FIG. 10 is a diagram illustrating an exemplary user interaction with a voice terminal service platform. The system allows a user 1030 to call in and use voice commands to navigate menus and further support phone notification applications. The voice platform is based on broad voice interaction that can be initiated in a push or pull mode such that the user 1030 may receive a notification about, for example, an email message and then has the ability to react and interact with the full system. The system also has the opportunity to interact with the user 1030 by alerting the user 1030 about offerings and coupons that are triggered in response according to the user 1030 geographic location or contacts regarding what the user is looking up (e.g., based on a current information request), for example, with the full service or just in some way contextually related. Push notifier 1000 provides a push mechanism to notify the user 1030 based on previous configurations that have triggered an alert so that there may be some reason to call or notify the user through, for example, the phone system or one of the other described notification method. Once contact is established by the push notifier 1000, a pull mechanism 1010 may inform the user that there is a waiting email message, a stock alert, or other information initiating an interaction with the user. In response to the user 1030 request for data, the system provides appropriate notification and the ability to then launch into the full menu system of the entire application platform. At the same time, an offerings module 1020 monitors the type of data requested, the type of data the user is interacting with and may interrupt and for example, offer coupons to the user. For example, if the user is dialing "411" to look up pizza restaurants, the system may notify the user of a special deal with a restaurant or mention a sponsorship. If the user declines to listen to additional announcements, processing continues on with the call flow.

Figure 11:
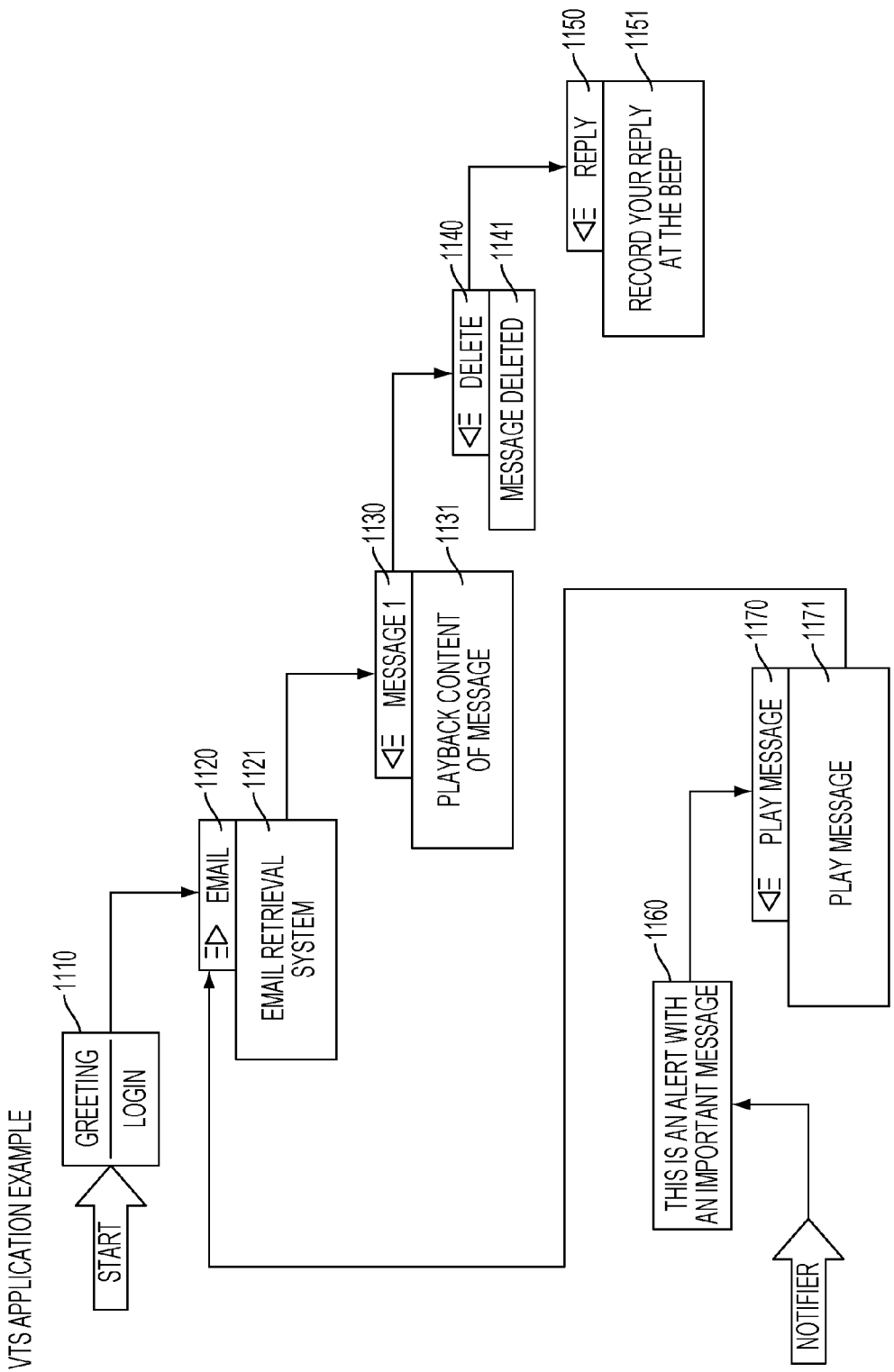
FIG. 11 is a diagram illustrating an exemplary voice terminal service fractional call flow.

FIG. 11 is a diagram illustrating an exemplary voice terminal service fractional call flow. This is a fractional call flow of voice terminal operation detailing how applications interact on the platform level. At block 1110 a session is initiated as an incoming call as the user is calling into the system. In response, the user receives a greeting. The user may then provide some login information to authenticate themselves as the user and then may have the opportunity to specify a desired function or capability, e.g., to say the command "e-mail" to launch the email application and at block 1121, initiate an email retrieval system. At block 1130, a message is played and the playback for the content of that message begins at block 1131. At block 1140, in response to receipt of a verbal "delete" command the message may be deleted at block 1141. At block 1150, in response to a reply command, the system executes at block 1151 such that the user may be allowed to record a voice message and send the reply message to the email origination and other recipients as a reply to the email. Meanwhile, at block 1160, an outgoing call may be initiated as an alert such that the system has called the end user, alerting the user that this is an alert with an important message. At block 1170, the user in may say "play message" to begin playback of the alert. At block 1171, the message is played back and, because the user is connected to the system, the user may be allowed to check the rest of their email (e.g., by saying "e-mail") and processing continues at block 1120. At block 1120 processing continues as would an incoming or "pull-based" portion of the application.

Figure 12:
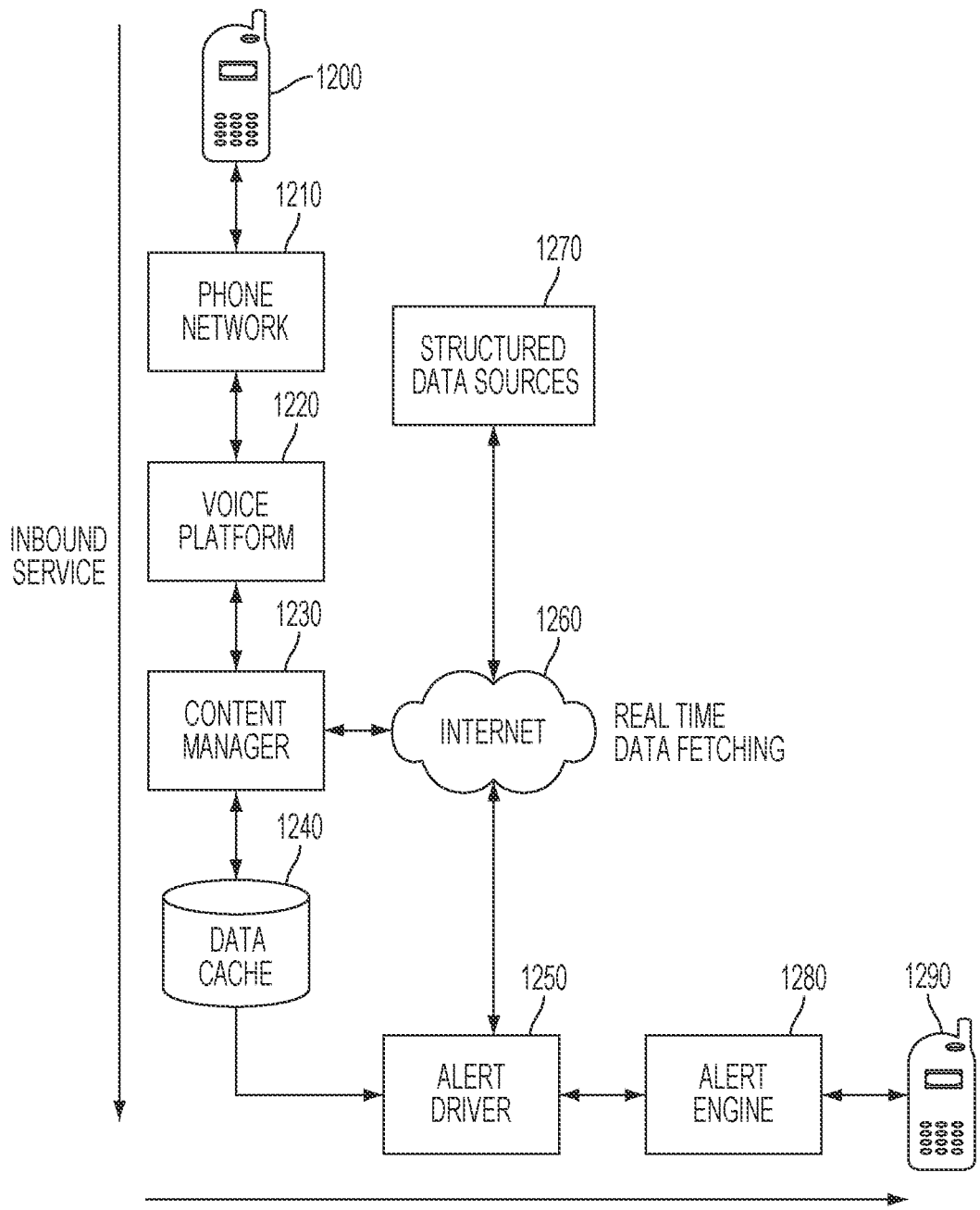
FIG. 12 is a diagram illustrating an exemplary voice terminal service architecture.

FIG. 12 is a diagram illustrating an exemplary voice terminal service architecture. Inbound calling service is initiated a calling node 1200, a telephone (or mobile phone) may be used by a user (e.g., user 704 of FIG. 7) to dial into the service via a telephone network 1210 or other communications means not necessarily limited to a phone network (e.g., Skype, a gaming system, or others.). A voice platform 1220 may include a speech processor available from Nuance Communications, Inc., Speechworks, IBM, Microsoft, Philips, Logvendo or others to provide data to a content management system 1230. The content management system 1230 merges user preferences and data sorting mechanisms along with the data pulled in from structured data sources on the, i.e., Internet sources 1260. A data cache 1240 provides a fast local storage mechanism for system data and can reduce (or eliminate) bandwidth issues when applicable. At the same time, the data cache 1240 can prevent or reduce the need to address other bandwidth and latency issues, which could cause unsatisfactory performance for the user. Processing continues at an alert driver 1250 to provide call switching. The data, once cached and merged with the contact manager, may be used for user interactions including triggering alerts to notify the user by calling them, interrupting an existing call session to let the person know there is an alert going on, or providing other notification functionality.

In one aspect of the disclosure, the user interaction may be based on real-time requests for new data or information. For example, real-time requests may be associated with volatile or time-sensitive data, such as a user's online calendar appointments, or various forms of social media information, during a call or telephone session. The alert driver 1250 may interact with data on the Internet to identify and provide structured data sources such as RSS feeds, text that is formatted in very specific ways, weather reports having a very specific structure, or others. Data may also be provided by private data sources, homeland security alerts and information, municipalities, police precincts, and other sources of, preferably, structured data. The alert driver 1250 feeds into an alert engine 1280, which contains rules and is a mechanism for deciding how to contact an end user. The alert engine 1280 may, for example, determine whether or not the system should attempt to contact a user based on certain rules, e.g., depending on their time of day preferences and where to contact the user if they have provided us multiple points of contact, multiple contact numbers, or others. For example, the alert engine 1280 may include an ability to spread a multiple destination with the same alert as may be useful use in an emergency scenario when it may be desirable to notify a group of "100 people" for a particular emergency. Alerts can be provided to a receiving node 1290 as voice messages.

The interactive voice access and retrieval of information system can be implemented in conjunction with an interactive voice access and notification system. In one aspect of the disclosure, the interactive voice access and notification system may support an electronic health record system that includes an alert capability. The electronic health record system may processes notification events provided or selected by a user. In one aspect of the disclosure, the notification events may relate to the health and/or well being of a family member. In this aspect of the disclosure, the electronic health record system queues automated telephone calls to a recipient or contact (e.g., a family member) during a current scheduled time triggered by a notification event for monitoring the health and/or well being of the family member.

In some aspects of the disclosure, an event monitoring system monitors one or more notification events associated with one or more contacts in a contact list or other arrangement of contacts received from a user. The event monitoring system monitors the one or more notification events to determine a trigger for the one or more notification events. The event monitoring system also initiates a call including an audible notification message to the one or more contacts based on the trigger for the one or more notification events. The event monitoring system further sends a confirmation response to the user when response information from the one or more contacts triggers a confirmation response.

Although the response information from the one or more contacts includes personal health record, the information or notification, e.g. confirmation response, sent to the user regarding the personal health record of the one or more contacts may be a generic message associated with the personal health record. The information may be generic to comply with Health Insurance Portability and Accountability Act (HIPAA) specifications. For example, the notification to the user may indicate that the call to the one or more contacts reports an out-of-range response. In some aspects of the disclosure, the interactive voice access and notification system may prompt the user to login to the secure web interface to view the personal health record stored in a Health Insurance Portability and Accountability Act (HIPAA) compliant database.

Figure 13:
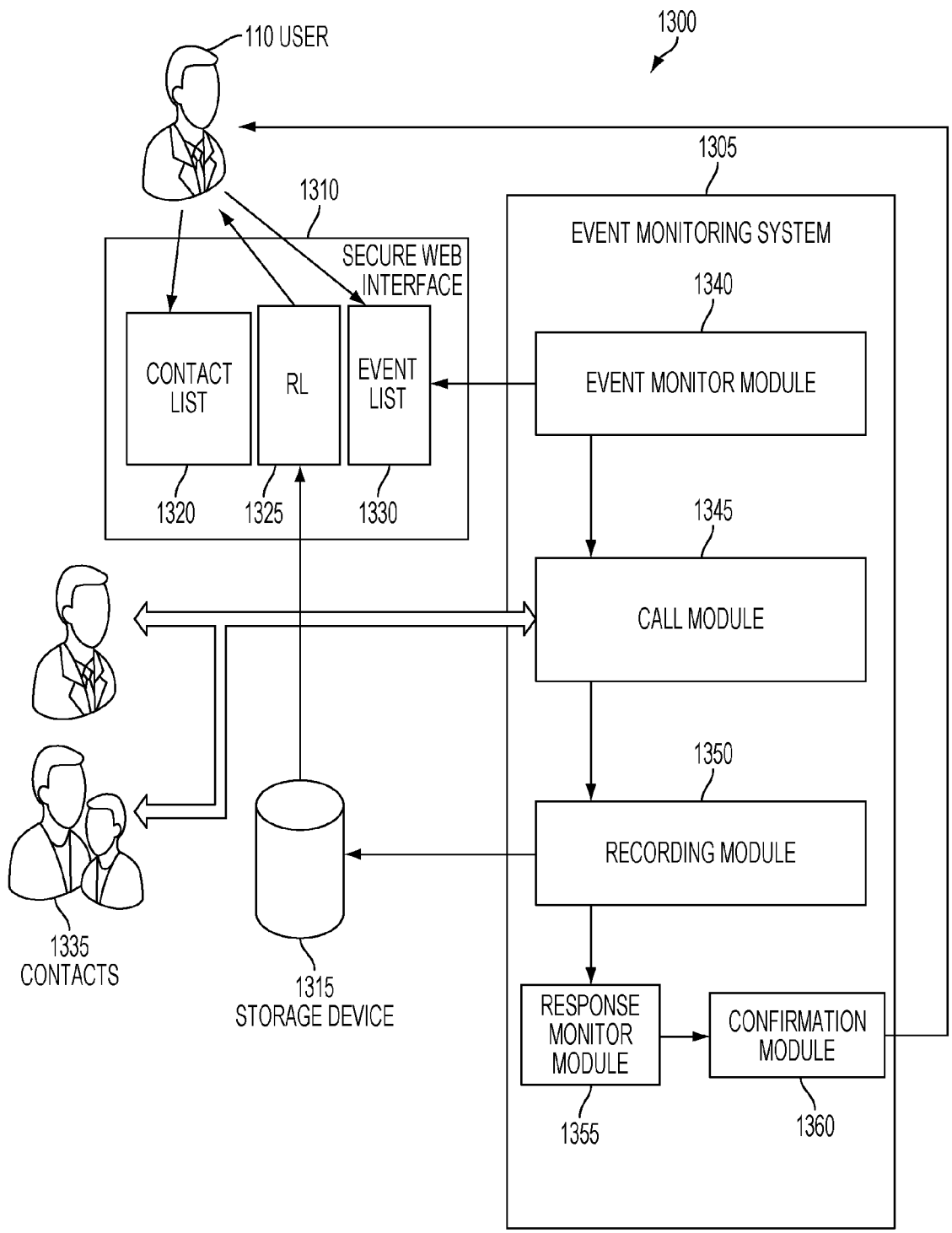
FIG. 13 is a block diagram illustrating an interactive voice access and notification system according to one aspect of the disclosure.

Although the interactive voice access and notification system illustrated by FIG. 13 is described with reference to an electronic health record system for monitoring the health of family members provided by a user, the system also applies to monitoring any contact provided by the user to improve the general well being of the contact. For example, the audible notification messages may be implemented to alert the contact to pay their rent, utility bill, send birthday or anniversary greetings or other non-health-related event.

FIG. 13 is a block diagram illustrating an interactive voice access and notification system 1300 according to one aspect of the disclosure. The system 1300 includes an event monitoring system 1305, an interface 1310 (e.g., web interface, computer-based user interface or a mobile device-based user interface) and a storage device 1315. The event monitoring system 1305 may be incorporated in a server implemented in the computer system 600, for example. The server may be a web-server for providing web services that supports the interface 1310 on a client (e.g., mobile device 112) or any application server that provides data to any other available interface method or application access method. In one aspect of the disclosure, the storage device 1315 and the event monitoring system 1305 are integrated in a single device. Alternatively, the storage device 1315 is independent but coupled to the event monitoring system 1305. The storage device may include a Health Insurance Portability and Accountability Act (HIPAA) compliant database. The event monitoring system 1305 includes an event monitor module 1340, a call module 1345, a recording module 1350, a response monitor module 1355, and a confirmation module 1360.

The interface 1310 is configured to receive information identifying one or more contacts including but not limited to, family members, friends and/or associates in an arrangement of contacts (e.g., a contact list 1320) from the user 110. The interface 1310 may also be configured to receive one or more events, (e.g., notification events) in an arrangement of notification events (e.g., event list 1330) from the user 110. In one aspect of the disclosure, the interface 1310 may be associated with a notifier, (e.g., notifier 104) to receive the notification events 106 from the user 110. The notifier may be integrated in the event monitoring system 1305 or may be independent but coupled to the event monitoring system 1305. The interface 1310 may be further configured to receive a response report based on a response from one or more contacts 1335. The response report may be arranged in a response list (RL) 1325 or other arrangement for display on the interface 1310. In one aspect of the disclosure, the response report may be received from the storage device 1315.

The contacts 1335 can be aging seniors living in their own homes at a distance from other family members. The user 110 or account owner creates the contact list 1320 of family members and friends who are eligible to receive the audible notification message. In one aspect of the disclosure, the creation of each new contact by the user triggers an authentication or notification rule either immediately or at a user-specified date and time. For example, a triggering module (not shown) triggers the authentication rule in response to an addition of a new recipient. The authentication rule includes a time for contacting the recipient, contact information for the recipient and/or an identification information for the recipient. The authentication rule may include calling the contact 1335, confirming the identity of the contact 1335, and/or requesting explicit permission to add the contact 1335 to the contact list 1320 for purposes of automated notification. In some aspects of the disclosure, each contact that is an HIPAA covered entity may be added to the contact list 1320 or be monitored without explicit permission. For example, pre-existing signed documentation allowing such contact with an HIPAA covered entity may already exist. The authentication rule may be part of a broader notification rule, e.g. notification rule 108. The notification rule 108 may be implemented to acquire and save health-related information of the contact 1335 in the storage device 1315. Sending messages from the user 110 to the contact 1335 in the contact list 1320 may be based on the successful authentication of the contact 1335. For example, the user may not send any further messages to the contact 1335 until, for example, the contact 1335 provides an approval.

The interface 1310 receives a notification event (e.g., the notification event 106 of FIG. 1) or a list of notification events associated with one or more contacts 1335. The notification event may be selected at the option of the user 110 or created by the user 110. Each notification event created or selected by the user 110 can generate one or more telephone calls to one or more contacts 1335 in the contact list 1320. The notification event may include a customized message from the user, a predetermined data collection dialog or the like. For example, a notification event may include instructions to call a family member in the contact list 1320 every morning, except Sunday, at 11:15 am. The notification event may also include reading a personal or customized message (e.g., pre-recorded by the user 110) asking a yes or no medication adherence question and recording a response, asking for and recording health related information including blood sugar reading, blood pressure reading, and asking for and recording any response (e.g., voice message) from the family member.

The predetermined data collection dialog may also include a set of confirmation criteria rules. For example, a confirmation criteria rule may indicate when a blood sugar reading of a family member is outside a predetermined range, over a predetermined number of days in a row. When this blood sugar reading event occurs, the confirmation criteria rule may facilitate notifying the user 110 or a predetermined contact (e.g., medical caregiver or medical emergency response entity) via an e-mail message, a telephone call, a voice mail message, a short message service (SMS) message, a pager alert, and/or a fax. The user 110 may also access the response information by accessing a secure web interface (e.g., interface 1310) and viewing the response. The response information may include medical related information of the contact 1335 including biometric measurement information, data measured by a medical device, diagnostic information and health status information of the contact 1335. In one aspect of the disclosure, the contact list and the list of notification events are maintained by the user 110 and are stored in the storage device 1315.

The event monitor module 1340 monitors the list of notification events to ensure that the notification events are implemented accordingly. In one aspect of the disclosure, the event monitor module 1340 processes the notification events, and queues automated telephone calls for a current scheduled time for one or more notification events. For example, the event monitor module 1340 affirms the current scheduled time (i.e., correct time, recurrence schedule, day of month, day of week etc.) of a notification event, affirms the validity of a contact 1335 in the contact list 1320 and affirms the validity of an audible notification message in preparation for the queuing of a telephone call to a contact 1335 in the contact list 1320. The call module 1345 initiates the call to the contact 1335 at an appropriate time affirmed by the event monitor module 1340. The call module 1345 identifies when the call is answered by a live person and when the call is answered by the intended contact 1335. The call may be re-queued when the call is not answered by a live person and/or when the call is not answered by the intended contact 1335. The status of the call is saved in the storage device 1315 and/or posted to the response list 1325 as an unsuccessful call. When the call module 1345 indicates the call is answered by the intended contact 1335, the audible notification message is read to the contact 1335 and the data collection dialogs are executed.

The response information received from the contact 1335 is recorded by a recording module 1350 and then stored in the storage device 1315. A list of responses from one or more contacts 1335 may be provided to the response list 1325 for display on the interface 1310. The response information is also monitored by the response monitor module 1355 to facilitate activation of any confirmation notification rules defined by the user 110. For example, the response monitor module 1355 may trigger a confirmation response when the medical related information provided by the one or more contacts is outside of a predetermined range. The confirmation notification rules may be part of a notification rule, e.g. notification rule 108. In one configuration, when a confirmation rule is triggered by any response from the contact 1335, a notification message is sent by the confirmation module 1360 to the user 110 via a specified communication channel. The specified communication channel may include an e-mail message, a voice mail message or telephone call, a pager alert, a short message service (SMS) message, a multimedia messaging service (MMS) message, a fax message, a push notification to mobile device application, or other communication channel. In this configuration, the notification message, which is based on the response information is monitored and processed to comply with HIPAA standards.

Figure 14:
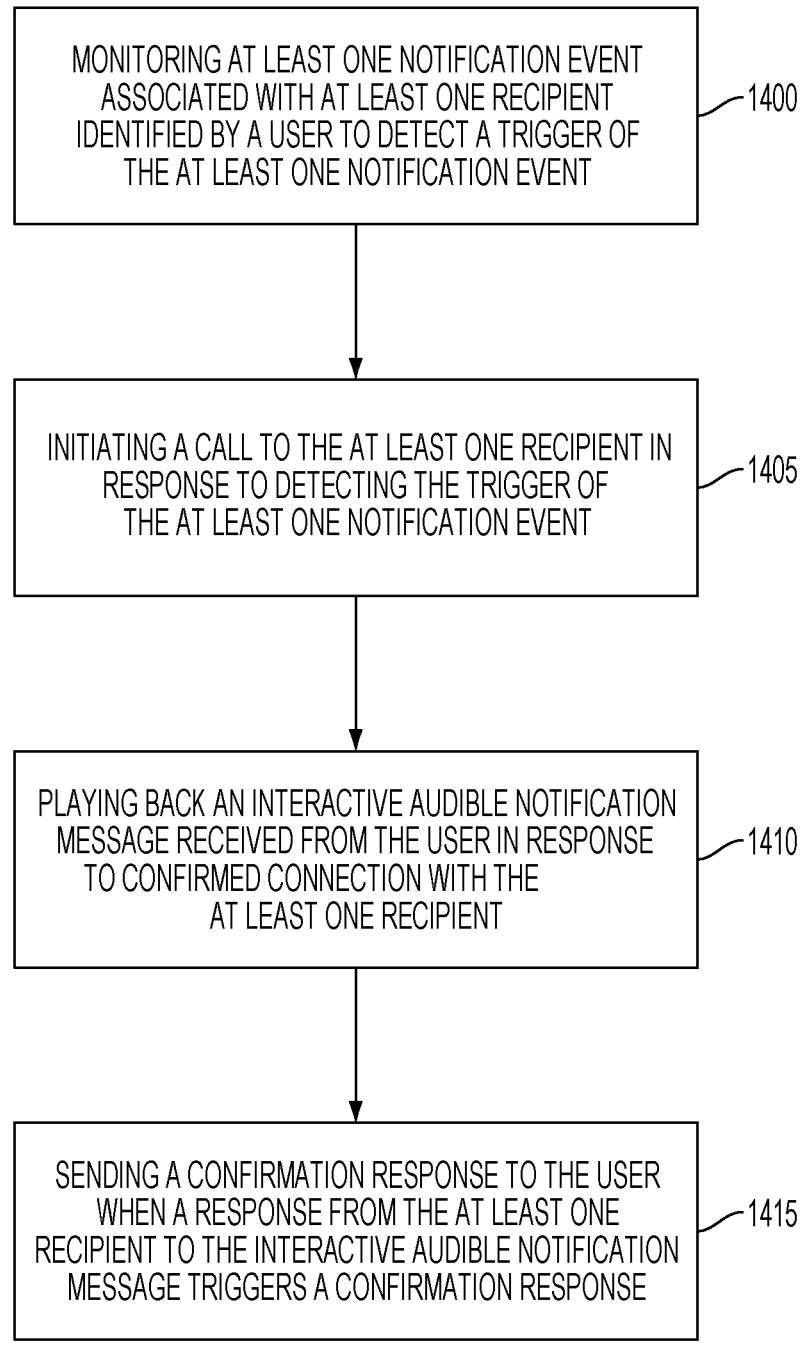
FIG. 14 shows an interactive voice access and notification method according to an aspect of the disclosure.

FIG. 14 shows an interactive voice access and notification method according to an aspect of the disclosure. The method includes monitoring one or more notification events associated with one or more recipients identified by a user at block 1400. The one or more notification events are monitored to detect a trigger of the one or more notification events. For example, as shown in FIG. 13, the event monitor module 1340 monitors the list of notification events to ensure the notification events are implemented accordingly. In one aspect, the event monitor module 1340 processes the notification events, and queues automated telephone calls for a current scheduled time. At block 1405, the method includes initiating a call to the one or more recipients in response to detecting the trigger of the one or more notification events. For example, as shown in FIG. 13, the call module 1345 initiates the call to the contact 1335 at an appropriate time affirmed by the event monitor module 1340. At block 1410, the method includes playing back an interactive audible notification message received from the user in response when it is confirmed the one or more contacts is on the line. For example, as shown in FIG. 13, when the call module 1345 indicates the call is answered by the intended contact 1335, the audible notification message is read to the contact 1335 and the data collection dialogs are executed. At block 1415, the method sends a confirmation response to the user when a response from the one or more recipients to the interactive audible notification message triggers a confirmation response. For example, as shown in FIG. 13, when a confirmation rule is triggered by a response from the contact 1335, a notification message is sent by the confirmation module 1360 to the user 110 via a specified communication channel.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. An interactive voice access and notification method, comprising:
    monitoring at least one notification event associated with at least one recipient identified by a user to detect a trigger of the at least one notification event;
    initiating a call to the at least one recipient in response to detecting the trigger of the at least one notification event, the call being initiated by a system;
    playing back an interactive audible notification message associated with the system initiated call to the at least one recipient of the call in response to confirming the at least one recipient of the call is on the line; and
    sending a confirmation response to the user when a response from the at least one recipient of the call to the interactive audible notification message triggers a confirmation response, the response from the at least one recipient comprising medical related information for the at least one recipient including at least one of biometric measurement information, data measured by a medical device, diagnostic information and health status information.

2. The method of claim 1, further comprising triggering a notification rule in response to addition of a new recipient, the notification rule including at least one of a time for contacting the new recipient, contact information for the new recipient and identification information for the new recipient.

3. The method of claim 1, further comprising triggering an out of range confirmation response when the medical related information provided by the at least one recipient is outside of a predetermined range.

4. An interactive voice access and notification method comprising:
    monitoring at least one notification event associated with at least one recipient identified by a user to detect a trigger of the at least one notification event;
    initiating a call to the at least one recipient in response to detecting the trigger of the at least one notification event, the call being initiated by a system;
    playing back an interactive audible notification message associated with the system initiated call to the at least one recipient of the call in response to confirming the at least one recipient of the call is on the line;
    sending a confirmation response to the user when a response from the at least one recipient of the call to the interactive audible notification message triggers a confirmation response; and at least one of
    requesting permission to add the at least one recipient to a contact list created by the user; and
    adding the at least one recipient who is covered-entity according to Health Insurance Portability and Accountability Act (HIPAA) without explicit permission.

5. An interactive voice access and notification method comprising:
    monitoring at least one notification event associated with at least one recipient identified by a user to detect a trigger of the at least one notification event;
    initiating a call to the at least one recipient in response to detecting the trigger of the at least one notification event, the call being initiated by a system;
    playing back an interactive audible notification message associated with the system initiated call to the at least one recipient of the call in response to confirming the at least one recipient of the call is on the line;
    sending a confirmation response to the user when a response from the at least one recipient of the call to the interactive audible notification message triggers a confirmation response;
    identifying that the call is answered by a live person; and
    confirming the live person is the at least one intended recipient based on an authentication rule.

6. An interactive voice access and notification apparatus, comprising:
    a memory; and
    at least one processor coupled to the memory and configured:
        to monitor at least one notification event associated with at least one recipient identified by a user to detect a trigger of the at least one notification event;
        to initiate a call to the at least one recipient in response to detecting the trigger of the at least one notification event, the call being initiated by a system;
        to play back an interactive audible notification message associated with the system initiated call to the at least one recipient of the call in response to confirming connection with the at least one recipient of the call; and
        to send a confirmation response to the user when a response from the at least one recipient of the call to the interactive audible notification message triggers a confirmation response, the response from the at least one recipient comprising medical related information for the at least one recipient including at least one of biometric measurement information, data measured by a medical device, diagnostic information and health status information.

7. The apparatus of claim 6, in which the at least one processor is further configured to trigger a notification rule in response to addition of a new recipient, the notification rule including at least one of a time for contacting the new recipient, contact information for the new recipient and identification information for the new recipient.

8. The apparatus of claim 6, in which the processor is further configured to trigger a confirmation response when the medical related information provided by the at least one recipient is outside of a predetermined range.

9. An interactive voice access and notification apparatus, comprising:
   a memory; and
   at least one processor coupled to the memory and configured:
   to monitor at least one notification event associated with at least one recipient identified by a user to detect a trigger of the at least one notification event;
   to initiate a call to the at least one recipient in response to detecting the trigger of the at least one notification event, the call being initiated by a system;
   to play back an interactive audible notification message associated with the system initiated call to the at least one recipient of the call in response to confirming connection with the at least one recipient of the call;
   to send a confirmation response to the user when a response from the at least one recipient of the call to the interactive audible notification message triggers a confirmation response; and at least one of
   to request permission to add the at least one recipient to a contact list created by the user and
   to add the at least one recipient who is a covered-entity according to Health Insurance Portability and Accountability Act (HIPAA) without explicit permission.

10. An interactive voice access and notification apparatus, comprising:
    a memory; and
    at least one processor coupled to the memory and configured:
    to monitor at least one notification event associated with at least one recipient identified by a user to detect a trigger of the at least one notification event;
    to initiate a call to the at least one recipient in response to detecting the trigger of the at least one notification event, the call being initiated by a system;
    to play back an interactive audible notification message associated with the system initiated call to the at least one recipient of the call in response to confirming connection with the at least one recipient of the call;
    to send a confirmation response to the user when a response from the at least one recipient of the call to the interactive audible notification message triggers a confirmation response;
    to identify that the call is answered by a live person; and
    to confirm the live person is the at least one intended recipient based on an authentication rule.

11. A computer program product for interactive voice access and notification, comprising:
    a computer-readable medium having non-transitory program code recorded thereon, the program code comprising:
    program code to monitor at least one notification event associated with at least one recipient identified by a user to detect a trigger of the at least one notification event;
    program code to initiate a call to the at least one recipient in response to detecting the trigger of the at least one notification event, the call being initiated by a system;
    program code to play back an interactive audible notification message associated with the system initiated call to the at least one recipient of the call in response to confirming connection with the at least one recipient of the call; and
    program code to send a confirmation response to the user when a response from the at least one recipient of the call to the interactive audible notification message triggers a confirmation response, the response from the at least one recipient comprising medical related information for the at least one recipient including at least one of biometric measurement information, data measured by a medical device, diagnostic information and health status information.

12. The computer program product of claim 11, further comprising program code to trigger a notification rule in response to addition of a new recipient, the notification rule including at least one of a time for contacting the new recipient, contact information for the new recipient and identification information for the new recipient.

13. The computer program product of claim 11, further comprising program code to trigger an out of range confirmation response when the medical related information provided by the at least one recipient is outside of a predetermined range.

14. A computer program product for interactive voice access and notification comprising:
    a computer-readable medium having non-transitory program code recorded thereon, the program code comprising:
    program code to monitor at least one notification event associated with at least one recipient identified by a user to detect a trigger of the at least one notification event;
    program code to initiate a call to the at least one recipient in response to detecting the trigger of the at least one notification event, the call being initiated by a system;
    program code to play back an interactive audible notification message associated with the system initiated call to the at least one recipient of the call in response to confirming connection with the at least one recipient of the call;
    program code to send a confirmation response to the user when a response from the at least one recipient of the call to the interactive audible notification message triggers a confirmation response; and
    program code to at least one of, request permission to add the at least one recipient to a contact list created by the user; and to add the at least one recipient who is covered-entity according to Health Insurance Portability and Accountability Act (HIPAA) without explicit permission.

15. A computer program product for interactive voice access and notification of comprising:
    a computer-readable medium having non-transitory program code recorded thereon, the program code comprising:
    program code to monitor at least one notification event associated with at least one recipient identified by a user to detect a trigger of the at least one notification event;

program code to initiate a call to the at least one recipient in response to detecting the trigger of the at least one notification event, the call being initiated by a system;

program code to play back an interactive audible notification message associated with the system initiated call to the at least one recipient of the call in response to confirming connection with the at least one recipient of the call;

program code to send a confirmation response to the user when a response from the at least one recipient of the call to the interactive audible notification message triggers a confirmation response;

program code to identify that the call is answered by a live person; and program code to confirm the live person is the at least one intended recipient based on an authentication rule.

* * * * *